(12) United States Patent
Al-Hashimi et al.

(10) Patent No.: US 8,498,823 B2
(45) Date of Patent: Jul. 30, 2013

(54) HIGH-THROUGHPUT ENSEMBLE-BASED DOCKING AND ELUCIDATION OF 3-DIMENSIONAL STRUCTURAL CONFORMATIONS OF FLEXIBLE BIOMOLECULAR TARGETS

(75) Inventors: Hashim M. Al-Hashimi, Ann Arbor, MI (US); Andrew Stelzer, Ann Arbor, MI (US); Ioan Andricioaei, Irvine, CA (US); Aaron Frank, Irvine, CA (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 13/120,064

(22) PCT Filed: Sep. 25, 2009

(86) PCT No.: PCT/US2009/058429
§ 371 (c)(1),
(2), (4) Date: Mar. 21, 2011

(87) PCT Pub. No.: WO2010/036927
PCT Pub. Date: Apr. 1, 2010

(65) Prior Publication Data
US 2011/0172981 A1     Jul. 14, 2011

Related U.S. Application Data

(60) Provisional application No. 61/194,291, filed on Sep. 26, 2008, provisional application No. 61/212,303, filed on Apr. 9, 2009.

(51) Int. Cl.
*G06F 19/00* (2006.01)
*G01N 31/00* (2006.01)

(52) U.S. Cl.
USPC .................................. 702/19; 702/27; 702/30

(58) Field of Classification Search
None
See application file for complete search history.

(56) References Cited

U.S. PATENT DOCUMENTS

2006/0160136 A1* 7/2006 Xiang et al. .................... 435/7.1
2007/0166730 A1* 7/2007 Menon et al. ..................... 435/6

OTHER PUBLICATIONS

Hansen et al. (Journal of the American Chemical Society (2007) vol. 129, pp. 16072-16082).*
Zhang Qi et al: "Resolving the motional modes that code for RNA adaptation." Science (New York, N.Y.) Feb. 3, 2006, vol. 311, No. 5761, pp. 653-656, XP002569548, ISSN: 1095-9203.
Dayie K T et al: "Theory and practice of nuclear spin relaxation in proteins." Annual Review of Physical Chemistry 1996, vol. 47, 1996, pp. 243-282, XP008119337, ISSN: 0066-426X.
International Search Report for PCT/US2009/058429, ISA/EP, Rijswijk, NL mailed Jun. 17, 2010 (5 pages).
Written Opinion of the ISA for PCT/US2009/058429, ISA/EP, Rijswijk, NL, mailed Jun. 17, 2010 (8 pages).
Alder et al., 'Phase transition for a hard sphere system', pp. 1208-1209, J. Chem. Phys. vol. 27 (1957).
Al-Hashimi et al., 'RNA dynamics: it is about time', pp. 1-13, 2008.
Bohacek et al., 'Definition and display of steric, hydrophobic, and hydrogen-bonding properties of ligand binding sites in protein using lee and richards accessible surface: validation of a high-resolution graphical tool for drug design', pp. 1671-1684, 1992.
Bohacek et al., 'Multiple highly diverse structures complementary to enzyme binding sites: results of extensive applicaiotn of a de Novo design method incorporating combinatorial growth', pp. 5560-5571, 1994.
Bohacek et al., 'The art and practice of structure-based drug design: A molecular modeling perspective', pp. 3-50, 1996.
Chen et al., 'Deciphering protein dynamiocs from NMR data using explicit structure sampling and selection', pp. 2300-2306, 2007.
Dayie et al., 'Theory and practice of nuclear spin relaxation in proteins', pp. 234-282, 1996.
Dethoff et al., 'Characterizing complex dynamics in the transactivation response element apical loop and motional correlations with the bulge by NMR, molecular dynamics, and mutagenesis', pp. 3906-3915, 2008.
Frank et al., 'Constructing RNA dynamical ensembles by combining MD and motionally decoupled NMR RDCs: new insights into RNA dynamics and adaptive ligand recognition', pp. 3670-3679, 2009.
Gillan, 'The molecular dynamics calculation of transport coefficients', pp. 362-366, 1991.
Hellinga et al., 'Construction of new ligand binding sites in proteins of known structure', pp. 787-803, 1991.
Hellinga et al., 'Construction of new ligand binding sites in proteins of known structures', pp. 763-785, 1991.
Kumar et at., 'Folding funnels and conformational transitions via hinge-bending motions', pp. 141-164, 1999.

(Continued)

*Primary Examiner* — Lori A Clow
(74) *Attorney, Agent, or Firm* — Harness, Dickey & Pierce, P.L.C.

(57) ABSTRACT

Methods for generating putative ligand structures capable of altering the activity of a target effector molecule comprise: constructing an elongated monomer of the target effector molecule; constructing a three dimensional model of the target effector molecule under the influence of elongation using empirical three dimensional data, the model including a conformation revealing the binding portion of the target effector molecule to a putative ligand structure; generating a plurality of computational models of the target effector molecule; filtering the plurality of computational models against the three dimensional model created experimentally using a reiterative simulation analysis algorithm operable to identify and select a plurality of computational models having a root-mean square deviation below a predetermined threshold when compared to the three dimensional model of the target effector molecule; screening a plurality of ligands to rank the binding strength of each ligand with the plurality of computational models selected and selecting one or more ligands based on the ranking.

29 Claims, No Drawings

OTHER PUBLICATIONS

Lindan et al., 'A molecular dynamics study of the thermal conductivity of $CaF_2$ and $UO_2$', pp. 3929-3939, 1991.

Ma et al., 'Folding funnels and binding mechanisms', pp. 713-720, 1999.

Musselman et al., 'iRED analysis of TAR RNA reveals motional coupling, long-range correlations, and a dynamical hinge', pp. 411-422, 2007.

Nudler, 'Flipping riboswitches', pp. 19-22, 2006.

Perez-Canadillas et al., 'Recent advances in RNA-protein recognition', pp. 53-58, 2001.

Ripka et al., 'Peptidomimetic design', pp. 441-452, 1998.

Sowdhamini et al., 'Protein three-dimensional structure and molecular recognition: a story of soft locks and keys', pp. 187-192, 1995.

Tsai, et al., 'Folding funnels, binding funnels, and protein function', pp. 1181-1190, 1999.

Tucker et al., 'Riboswitches as versatile gene control elements', pp. 342-348, 2005.

Zhang et al., 'Resolving the motional modes that code for RNA adaptation', pp. 653-656, 2006.

Zhang, et al., 'Visualizing spatially correlated dynamics that directs RNA conformational transitions', pp. 1263-1268, 2007.

Zhang, et al., 'Extending the NMR spatial resolution limit for RNA by motional couplings', pp. 243-245, 2008.

\* cited by examiner

SEQUENCE LISTING

```
<160> NUMBER OF SEQ ID NOS: 10

<210> SEQ ID NO 1
<211> LENGTH: 15
<212> TYPE: RNA
<213> ORGANISM: Artificial Sequence
<220> FEATURE:
<223> OTHER INFORMATION: Nucleotide sequence of an RNA target effector
      sequence kink.

<400> SEQUENCE: 1
ucugagcuuc ggcuc                                                          15

<210> SEQ ID NO 2
<211> LENGTH: 24
<212> TYPE: RNA
<213> ORGANISM: Artificial Sequence
<220> FEATURE:
<223> OTHER INFORMATION: Nucleotide Sequence Of An RNA Target Effector
      Sequence Kink
<220> FEATURE:
<221> NAME/KEY: misc_feature
<222> LOCATION: (6)..(9)
<223> OTHER INFORMATION: n denotes a nucleotide of the target effector
      molecule being examined

<400> SEQUENCE: 2
ggacunnnnu cugagcuucg gcuc                                                24

<210> SEQ ID NO 3
<211> LENGTH: 51
<212> TYPE: RNA
<213> ORGANISM: Artificial Sequence
<220> FEATURE:
<223> OTHER INFORMATION: Nucleotide Sequence Of An RNA Target Effector
      Sequence Kink
<220> FEATURE:
<221> NAME/KEY: misc_feature
<222> LOCATION: (3)..(12)
<223> OTHER INFORMATION: n denotes random nucleotides selected from A,
      T, C, G, and U
<220> FEATURE:
<221> NAME/KEY: misc_feature
<222> LOCATION: (13)..(18)
<223> OTHER INFORMATION: n denotes a nucleotide of the target effector
      molecule being examined
<220> FEATURE:
<221> NAME/KEY: misc_feature
<222> LOCATION: (34)..(39)
<223> OTHER INFORMATION: n denotes a nucleotide of the target effector
``` molecule being examined
<220> FEATURE:
<221> NAME/KEY: misc_feature
<222> LOCATION: (40)..(49)
<223> OTHER INFORMATION: n denotes random nucleotides selected from A,
      T, C, G, and U

<400> SEQUENCE: 3
ggnnnnnnnn nnnnnnnnuc ugagcuucgg cucnnnnnnn nnnnnnnnnc c          51

<210> SEQ ID NO 4
<211> LENGTH: 38
<212> TYPE: RNA
<213> ORGANISM: Artificial Sequence
<220> FEATURE:
<223> OTHER INFORMATION: Nucleotide Sequence Of An RNA Target Effector
      Sequence Kink
<220> FEATURE:
<221> NAME/KEY: misc_feature
<222> LOCATION: (7)..(16)
<223> OTHER INFORMATION: n denotes random nucleotides selected from A,
      T, C, G, and U
<220> FEATURE:
<221> NAME/KEY: misc_feature
<222> LOCATION: (25)..(34)
<223> OTHER INFORMATION: n denotes random nucleotides selected from A,
      T, C, G, and U

<400> SEQUENCE: 4
ucugagnnnn nnnnnngcuu cggcnnnnnn nnnngcuc                         38

<210> SEQ ID NO 5
<211> LENGTH: 50
<212> TYPE: RNA
<213> ORGANISM: Artificial Sequence
<220> FEATURE:
<223> OTHER INFORMATION: Nucleotide Sequence Of An RNA Target Effector
      Sequence Kink
<220> FEATURE:
<221> NAME/KEY: misc_feature
<222> LOCATION: (3)..(12)
<223> OTHER INFORMATION: n denotes random nucleotides selected from A,
      T, C, G, and U
<220> FEATURE:
<221> NAME/KEY: misc_feature
<222> LOCATION: (13)..(18)
<223> OTHER INFORMATION: n denotes a nucleotide of the target effector
      molecule being examined
<220> FEATURE:
<221> NAME/KEY: misc_feature
<222> LOCATION: (33)..(38)
<223> OTHER INFORMATION: n denotes a nucleotide of the target effector
      molecule being examined
<220> FEATURE:
<221> NAME/KEY: misc_feature
<222> LOCATION: (39)..(48)
<223> OTHER INFORMATION: n denotes random nucleotides selected from A,
      T, C, G, and U

<400> SEQUENCE: 5
ggnnnnnnnn nnnnnnnnuu gagcuucggc ucnnnnnnnn nnnnnnnncc            50

<210> SEQ ID NO 6
<211> LENGTH: 27
<212> TYPE: RNA
<213> ORGANISM: Artificial Sequence
<220> FEATURE:
<223> OTHER INFORMATION: Nucleotide Sequence Of An RNA Target Effector
      Sequence Kink
<220> FEATURE:
<221> NAME/KEY: misc_feature
<222> LOCATION: (12)..(19)
<223> OTHER INFORMATION: n denotes a nucleotide of the target effector
      molecule being examined -continued

<400> SEQUENCE: 6
ggcagaucug annnnnnnnu cucugcc                                              27

<210> SEQ ID NO 7
<211> LENGTH: 33
<212> TYPE: RNA
<213> ORGANISM: Artificial Sequence
<220> FEATURE:
<223> OTHER INFORMATION: Nucleotide Sequence Of An RNA Target Effector
      Sequence Kink
<220> FEATURE:
<221> NAME/KEY: misc_feature
<222> LOCATION: (15)..(22)
<223> OTHER INFORMATION: n denotes a nucleotide of the target effector
      molecule being examined

<400> SEQUENCE: 7
ggacucagau cugannnnnn nnucucugag ucc                                       33

<210> SEQ ID NO 8
<211> LENGTH: 51
<212> TYPE: RNA
<213> ORGANISM: Artificial Sequence
<220> FEATURE:
<223> OTHER INFORMATION: Nucleotide Sequence Of An RNA Target Effector
      Sequence Kink
<220> FEATURE:
<221> NAME/KEY: misc_feature
<222> LOCATION: (3)..(12)
<223> OTHER INFORMATION: n denotes random nucleotides selected from A,
      T, C, G, and U
<220> FEATURE:
<221> NAME/KEY: misc_feature
<222> LOCATION: (24)..(31)
<223> OTHER INFORMATION: n denotes a nucleotide of the target effector
      molecule being examined
<220> FEATURE:
<221> NAME/KEY: misc_feature
<222> LOCATION: (40)..(49)
<223> OTHER INFORMATION: n denotes random nucleotides selected from A,
      T, C, G, and U

<400> SEQUENCE: 8
ggnnnnnnnn nnggcagauc ugannnnnnn nucucugccn nnnnnnnnnc c                   51

<210> SEQ ID NO 9
<211> LENGTH: 51
<212> TYPE: RNA
<213> ORGANISM: Artificial Sequence
<220> FEATURE:
<223> OTHER INFORMATION: Nucleotide Sequence Of An RNA Target Effector
      Sequence Kink
<220> FEATURE:
<221> NAME/KEY: misc_feature
<222> LOCATION: (14)..(23)
<223> OTHER INFORMATION: n denotes random nucleotides selected from A,
      T, C, G, and U
<220> FEATURE:
<221> NAME/KEY: misc_feature
<222> LOCATION: (24)..(31)
<223> OTHER INFORMATION: n denotes a nucleotide of the target effector
      molecule being examined
<220> FEATURE:
<221> NAME/KEY: misc_feature
<222> LOCATION: (32)..(41)
<223> OTHER INFORMATION: n denotes random nucleotides selected from A,
      T, C, G, and U

<400> SEQUENCE: 9
ggcagaucug agcnnnnnnn nnnnnnnnnn nnnnnnnnnn ngcucucugc c                   51

-continued

```
<210> SEQ ID NO 10
<211> LENGTH: 50
<212> TYPE: RNA
<213> ORGANISM: Artificial Sequence
<220> FEATURE:
<223> OTHER INFORMATION: Nucleotide Sequence Of An RNA Target Effector
      Sequence Kink
<220> FEATURE:
<221> NAME/KEY: misc_feature
<222> LOCATION: (3)..(12)
<223> OTHER INFORMATION: n denotes random nucleotides selected from A,
      T, C, G, and U
<220> FEATURE:
<221> NAME/KEY: misc_feature
<222> LOCATION: (23)..(30)
<223> OTHER INFORMATION: n denotes a nucleotide of the target effector
      molecule being examined
<220> FEATURE:
<221> NAME/KEY: misc_feature
<222> LOCATION: (39)..(48)
<223> OTHER INFORMATION: n denotes random nucleotides selected from A,
      T, C, G, and U

<400> SEQUENCE: 10
ggnnnnnnnn nnggcagauu gannnnnnnn ucucugccnn nnnnnnnncc                50
```

HIGH-THROUGHPUT ENSEMBLE-BASED DOCKING AND ELUCIDATION OF 3-DIMENSIONAL STRUCTURAL CONFORMATIONS OF FLEXIBLE BIOMOLECULAR TARGETS

RELATED APPLICATIONS

This application is a 371 U.S. National Stage of International Application No. PCT/US2009/058429, filed Sep. 25, 2009. This application claims priority to U.S. Provisional Application No. 61/194,291, filed on Sep. 26, 2008, and U.S. Provisional Application No. 61/212,303, filed on Apr. 9, 2009. The contents of both priority applications are incorporated herein in their entirety.

GOVERNMENT RIGHTS

This invention was made with government support under grants RO1 AI066975 awarded by the National Institutes of Health and MCB0644278 and CHE0548047 awarded by the National Science Foundation. The government has certain rights in the invention.

FIELD

The present technology relates to methods for identifying in high throughput fashion, small molecules likely to bind to target effector molecules and thereby alter biological activity of the target effector molecule. The present technology also relates to methods for constructing atomic resolution dynamic ensembles with timescale sensitivity extending up to milliseconds, to study the interaction between small molecules and nucleic acids.

BACKGROUND

This section provides background information related to the present technology which is not necessarily prior art.

In various biological processes, the specific binding of a target effector molecule to some ligand or small molecule drug compound results in some effect to biological activity. The binding might constitute part of a signaling mechanism between cells, it might be part of a mechanical operation such as muscle contraction, or it might mediate a catalytic event, or it might be part of yet another process. One way that drugs can work is competitive inhibition: binding to a target effector molecule more strongly than their natural binding partners, and thereby interrupting whatever process the target effector molecule mediates. Drugs can exert their effects using an allosteric mechanism, where they bind to an effector molecule and change its properties so that it can no longer perform native function(s).

When considering a target effector molecule and an arbitrary small organic molecule, it is useful to determine computationally, whether the small molecule will bind to the target effector molecule, and if so, it is useful to estimate the geometry of the bound complex, as well as the affinity of the binding. Most molecular binding algorithms include two components: a search technique to find the optimal placement of the ligand in the binding region of the target effector molecule, and a scoring function to rate each placement, as well as to rank candidate ligands against each other.

One of the critical questions for structural chemists and biologists is, how can a representative subset of the conformational ensemble typical of a given effector target molecule be obtained? Currently there exists only a limited set of means to generate static snap-shots of the three dimensional structure of macromolecules and there are no experimental methods for generating atomic movies and dynamic ensembles of structure with timescales sensitivity extending up to milliseconds. Static snap-shots of structure can be determined experimentally either from X-ray crystallography or NMR; dynamic ensembles can be generated via computational methods such as Monte Carlo (MC) or Molecular Dynamics (MD) simulations. Simulations typically use as a starting point a static snap-shot of the structure determined by one of the experimental methods. Ideally, the sampling used provides the most extensive coverage of the structure space. Comparisons done between traditional molecular simulations and experimental techniques seem to indicate that X-ray crystallography NMR structures seem to provide better coverage. Although experimental data is preferable, it is currently impossible to obtain the required amount of data needed to determine movies and dynamic ensembles at atomic resolution. A second critical question is, given a movie capturing comprising hundreds of thousands to millions of structures, what is the best way of combining this large amount of structural information for a docking study? This question also remains open. Current approaches use diverse ways of combining multiple structures.

As an exemplary target effector molecule, many non-coding RNAs perform their biological functions by undergoing large changes in conformation in response to specific cellular signals including the recognition of proteins, nucleic acids, metal ions, metabolites, vitamins, changes in temperature, and even RNA biosynthesis itself. J. M. Perez-Canadillas and G. Varani, *Curr. Opin. Struct. Biol.* 11 (1), 53 (2001). B. J. Tucker and R. R. Breaker, *Curr Opin Struct Biol* 15 (3), 342 (2005). E. Nudler, *Cell* 126 (1), 19 (2006). H. M. Al-Hashimi and N. G. Walter, *Curr Opin Struct Biol In* Press (2008). C. Musselman, H. M. Al-Hashimi, and I. Andricioaei, *Biophys J* 93 (2), 411 (2007). These conformational transitions guide RNA folding during co-transcriptional folding; provide the molecular basis for sensing and signaling transactions that allow riboswitches to regulate gene expression in response to changes in environmental conditions; allow ribozymes to dynamically meet the diverse structural requirements associated with their multi-step catalytic cycles; and enable complex ribonucleoproteins to assemble in a hierarchical and sequentially ordered manner.

Although it is clear that many non-coding RNAs (ncRNAs) undergo large changes in structure in order to carry out their function, the mechanism by which these conformational transitions occurs remains poorly understood. An intense area of investigation focuses on whether cellular factors such as proteins and ligands act catalytically to induce the RNA conformational change via 'induced fit', or they select and bind distinct RNA conformers from a pre-existing dynamical ensemble via 'conformational selection'. Insights into such mechanistic questions have been impeded by lack of biophysical techniques that allow the 3D visualization of intrinsic RNA dynamics over biologically relevant timescales.

Recently, "conformational selection" from dynamical ensembles has emerged as a mechanism that rationalizes how different ligands bind different structures of the RNA receptor without necessitating either the "lock and key" or "induced fit" mechanisms. See Kumar et al. (1999) Cell Biochem. and Biophys. 31:141-164; Ma et al. (1999) Protein Eng. 12:713-720; Tsai et al. (1999) Protein Sci. 8:1181-1190. This mechanism assumes that macromolecules exist in solution as multiple, equilibrating conformations. These various conformations can be described by mechanical laws, using standard statistical distributions. The process of ligands binding to the receptors thus shifts the equilibrium from the statistical distribution of native conformations when the ligand is absent, to a new equilibrium that includes the receptor-ligand conformation. In this view, ligands bind to an ensemble of pre-existing receptor conformations. Ligand binding then shifts the overall dynamic equilibrium to stabilize the conformation present in the receptor-ligand complex.

This concept of conformationally mobile receptors (and ligands) is not new, but arose shortly after the discovery of modern conformational analysis. Previous thoughts on this topic posited that "the conformation of an enzyme in solution is regarded to be a statistical average of a number of conformations, the protein structure oscillating between these conformations." Straub (1964) Advan. Enzymol. 26:89-114. Since then, the conformational mobility of biologically active proteins has been repeatedly demonstrated via biophysical methods.

Nevertheless, due to computational limitations, current molecular modeling and drug design efforts treat proteins and other biomolecules as static models even though they are clearly dynamic macromolecular structures, constantly in motion. In general, the static models portray either the native protein conformation or the protein conformation tightly bound to a potent peptide-derived inhibitor. Some modeling studies accommodate small changes in protein and ligand side chain conformations or hydrogen bonding interactions. This approach, called the "soft lock and key" model has subsequently been utilized to modify inhibitor design. Sowdhamini et al. (1995) Pharm. Acta Helv. 69:185-192.

But other protein conformations including ones that are significantly altered by motions that occur at timescales inaccessible to simulations are not considered when designing or modifying enzyme inhibitors, in spite of the fact that biophysical methods have established their existence, because their structural characteristics cannot in general be determined a priori with the required atomic resolution.

The atomic resolution characterization of dynamics in complex biomolecules is currently a major challenge in structural biology and biophysics. NMR spectroscopy is one of the most powerful techniques for characterizing dynamics uniquely providing comprehensive information regarding the amplitude, timescale and—in favorable cases—direction of motions with site-specific resolution. However, even with abundant measurements that can be made with the use of NMR, the total number of observables still pale in comparison to the total number of parameters needed to fully describe dynamics. MD simulations provide an all-atom description of dynamics; however, force fields remain to be thoroughly validated particularly for nucleic acids and simulation timescales remain limited to ~100 nanoseconds (ns). Because they are complementary on the spatial and temporal scales, the limitations inherent to nuclear magnetic resonance (NMR) and MD could in principle be overcome by combining the two techniques; MD can fill the shortage in NMR data and NMR can provide a means for validating and potentially correcting force fields and accelerate MD conformational sampling to millisecond timescales.

There remains a long-felt and unmet need to resolve these dynamic conformations as a means to yield information that leads to the rational design of targeted, biologically-active compounds.

One of the goals of the present technology is to use NMR derived validation of target effector molecule structure and computer derived docking as a way to prioritize combinatorial library screening efforts.

SUMMARY

This section provides a general summary of the present technology, and is not a comprehensive disclosure of its full scope or all of its features.

The present technology provides methods for collecting data on the motion and conformations of a target effector molecule, which is akin to taking a snapshot of a structural conformer of the target effector molecule. The method allows taking snapshots of the target effector structure from every possible angle and thus provides the maximum resolution of the target effector molecule structure using NMR data and MD simulation.

In another aspect, the present technology provides methods for analyzing the structural conformations of a target effector molecule that can be targeted with a small molecule, the method comprising:

a) providing a target effector molecule having an artificial elongated sequence having one or more variable kinks;

b) obtaining residual anisotropic interactions, spin relaxation, relaxation dispersion and paramagnetic relaxation enhancement data from the target effector molecule having said elongated structure;

c) creating a plurality of atomic-resolution dynamical ensembles reflecting motional trajectories of the target effector molecule;

d) selecting one or more of the dynamical sub-ensembles using a computational simulation algorithm, for example, Monte Carlo and other computational simulation, to generate a plurality of conformers that satisfy the residual anisotropic interactions and spin relaxation data;

e) identifying the one or more dominant conformers from the dynamical ensembles that can be targeted by a small molecule; and f) selecting and outputting the dominant conformers and motional trajectories of said target effector molecule that can be targeted by the small molecule.

In some embodiments, the method also includes one or more of the following:

constructing an elongated monomer of the target effector molecule;

constructing a three dimensional model of the target effector molecule under the influence of elongation using empirical three dimensional data, the model including a conformation revealing the binding portion of the target effector molecule to a putative ligand structure;

generating a plurality of computational models of the target effector molecule;

filtering the plurality of computational models against the three dimensional model created experimentally using a reiterative simulation analysis algorithm operable to identify and select a plurality of computational models having a root-mean square deviation below a predetermined threshold when compared to the three dimensional model of the target effector molecule;

screening a plurality of ligands to rank the binding strength of each ligand with the plurality of computational models selected, and selecting one or more ligands based on the ranking.

In another aspect, the ligand and computational model selected in the filtering step can be allowed to relax and readjust before calculating the relative binding affinity of the ligand to the computational model.

The target effector molecule can include a polypeptide, a protein, a polysaccharide, a nucleic acid (RNA, DNA, nucleic acid/peptide hybrids and nucleic acid mimetics), a lipid, a glycoprotein, or a glycolipid, each of the target effector molecules having one or more target effector sequences that confer some biological activity, for example, a recognition domain or motif, a binding recognition domain or motif or a catalytic domain or motif. The target effector sequence present in the target effector molecule can interact, bind, cleave, or otherwise interact with a ligand or other small molecule or factor. The target effector sequences can range in size from 2-1000 nucleotides, amino acids or other structural units.

In some embodiments, structural data calculated from computer simulations of molecular dynamics along with NMR residual dipolar couplings (RDCs) can be used to enhance the ability to provide snapshots (structural conformers) of all of the target effector MD. The ability to capture in high definition or maximum resolution all of the snapshots of the target effector molecule enables one to enhance the success rate of identifying or predicting more selective and specific binding ligands, drugs or small molecules that can bind to the target effector molecule. The present methods overcome the inherent difficulty in the field of molecular design to resolve the maximum number of twenty-five motionally averaged Wigner rotation elements which can theoretically be determined for chiral domains from RDC measurements.

Moreover, the present methods are advantageous in that the method provides the maximum spatial resolution of the target effector molecule by accessing five independent motionally decoupled alignments of the target effector molecule. This decoupling and access to the full complement of alignments enables the identification of target effector conformers that can be used to design small molecule drugs that can target a broader array of structures embodied by the target effector molecule, in other words, the method of the present disclosure defines structures of the target effector molecule that are operable to bind to a putative small molecule drug or other ligand. In addition having a full complement of possible structures permits the design of riboswitches and the like, for example, in RNA targets.

Further areas of applicability will become apparent from the description provided herein. The description and specific examples in this summary are intended for purposes of illustration only and are not intended to limit the scope of the present disclosure.

DETAILED DESCRIPTION

In some embodiments of the present technology, a method for analyzing the structural conformations of a target effector molecule is provided. RNA derived target effector molecules are difficult to analyze in solution due to the high flexibility of nucleic acids. The range of internal motion of the RNA target effector molecule can contribute to overall motion in inert ordered media. Herein is described a method where the target effector molecule has an artificial elongated sequence comprising one or more variable kinks. The elongation of the target effector molecule serves to reduce the contribution of internal motion to overall motion, so that they are, in effect, decoupled.

A domain-elongation strategy is introduced for decoupling internal and overall motions in RNA. In this approach, a target helix is elongated so that the overall motion is slowed down relative to internal motions and rendered less sensitive to internal fluctuations in other parts of the molecule. The elongation also simplifies analysis of NMR spin relaxation and residual dipolar coupling (RDC) data because it predefines the overall diffusion or alignment tensor to be axially symmetric with principal axis oriented nearly parallel to the elongated helix axis. Elongated RNAs are ideally suited for computing NMR observables from a given MD trajectory of a corresponding non-elongated RNA in which snapshots are aligned by superimposing the reference elongated helix.

With this method, an elongated target effector molecule is analyzed for RDC interactions and spin relaxation data by NMR or X-ray crystallography. This step of the method can be done with or without the presence of a ligand bound to the target effector molecule. If the method is performed in the presence of a ligand, the data collected will show the favored conformations of the binding site of the target effector molecule to be those engaged in the binding event. If the method is not performed in the presence of a ligand, the data will show the lowest energy solution phase conformations.

Next, molecular modeling simulations are performed on the target effector molecule and a plurality of atomic-resolution dynamical ensembles reflecting motional trajectories are obtained. This is accomplished by constructing computational models of the target effector molecule using computer modeling programs such as Molecular Dynamics, Monte Carlo, CHARMM (Chemistry at HARvard Macromolecular Mechanics is a name for a set of force fields for molecular dynamics and the name of the molecular dynamics simulation and analysis software package associated with them), FELIX, QUANTA, and GrowMol, or combinations thereof. From this data, a plurality of dynamical sub-ensembles of the target effector molecule can be selected using a computational simulation algorithm, for example, Monte Carlo simulation, among others, and a plurality of conformers that satisfy the residual anisotropic interactions and spin relaxation data obtained by NMR (or X-ray crystallography) are generated.

A plurality of dominant conformers from the dynamical ensembles can now be identified with the product of the method being a molecular model of the dominant conformers and solution-phase motional trajectories of the target effector molecule.

Furthermore, when performed in the presence of a ligand with affinity for the target effector molecule, the dominant conformers will be those conformers that simulate low-energy ligand complexation. This information can then be used to perform in silico screening of millions of putative ligand structures, with each individual ligand receiving a score, the score being indicative of in silico binding affinity. Structures can then be selected for synthesis and further research based on this score.

The terminology used herein is for the purpose of describing particular example embodiments only and is not intended to be limiting. As used herein, the singular forms "a", "an" and "the" may be intended to include the plural forms as well, unless the context clearly indicates otherwise. Thus, for example, reference to "a ligand" includes mixtures of ligands; reference to "an NMR resonance" includes more than one resonance, and the like. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

In some embodiments, the present technology provides for methods for accurately defining conformational ensembles of target effector molecules for use in rational design and identification of lead compounds.

As used herein, the term "target effector molecule" describes a molecule that can be selected from any biological molecule which is activated or inhibited by ligand binding to a recognition domain on the molecule. Target effector molecules encompassed by the present technology can include a diverse array of compounds including proteins, polypeptides, oligopeptides, polysaccharides and nucleic acids, including RNA and DNA. Exemplary proteins can include enzymes, transmembrane transporters, signal receptors and mediators, primary and secondary messengers, transcription and translation factors, and others. In a preferred method for practicing the technology isotopically labeled molecules are used for the target effector molecule, and substitute for the naturally occurring target effector molecule.

As used herein, the term "ligand" describes any naturally occurring or synthetic compound, or fragment thereof, that binds to the recognition domain of a target effector molecule. In some embodiments, the ligand can be a small organic molecule. Some of these small molecules are part of a larger collection of molecules found in combinatorial libraries. Ligands of the present technology also include members of combinatorial libraries of natural or synthetic small molecules, wherein the libraries contain tens, hundreds, thousands and hundred of thousands of variant species. Recognition domains include both primary binding domains and regulatory domains. Ligands can thus be analogs of known substrates or inhibitors or regulators of biological activity. They can also be compounds with no previously identified biological effect. Inhibitor analogs, substrate analogs and regulator analogs can be covalently linked to one another or to any class of ligand to enhance activity by the process of this invention. Binding between ligand and target effector molecule can be any form that causes the desired activation or inhibition, and includes ionic bonding, hydrogen bonding, and Van der Waals association.

As used herein, the "recognition domain" of a target effector molecule describes the local site of the target effector molecule to which a ligand binds and promotes modification of the target effector molecule's biological activity. This modification can be described as agonist activity or antagonist activity, depending on the circumstances of a particular ligand binding event.

As used herein, the "five order tensor elements" describe the partial alignment of a chiral molecular fragment relative to the magnetic fields.

As used herein, the "five independent motionally decoupled alignments" describe five alignments that yield five independent sets of RDC and RCSA data that can be used to determine all twenty-five Wigner elements $\langle D_{0i}^2(\alpha\beta)\rangle$.

As used herein, the "five motionally averaged Wigner rotation elements $\langle D_{0i}^2(\alpha,\beta)\rangle_n$ describe the partial alignment of a chiral molecular fragment relative to the magnetic field.

As used herein, "elongated" in reference to the target effector molecule refers to a modified target effector molecule whose structure has been physically extended (for example, an RNA molecule with 5-2000 extra C-G/G-C or A-T/T-A base pairs extended onto the terminus).

As used herein, the phrase "elongation sequence" is used to describe portion of the helix of an elongated RNA target effector molecule that includes only the added base pairs.

As used herein, the term "kink" or variations thereof can include the introduction of a chemical perturbation to the elongated helix which leads to a static or dynamic change in the orientation of the elongated helix axis relative to the RNA receptor molecule.

As used herein, the term "bulge" is that portion of a nucleic acid strand for which there is no complementary bases on the opposing strand.

As used herein, the term "internal loop" is a bulge, wherein some bases within the bulge find their complementary base so that the structure forms a hairpin shape.

As used herein, the term "n-way junction" is a joining section of nucleic acid wherein the n-way junction consists of n connecting helices.

As used herein, the term "dynamical ensembles" refers to computer data that describes those discrete conformations which a target effector molecule favors in the solution phase.

Individual ligands for screening can be selected inter alia on the basis of size and molecular diversity. Compounds in the collection or library can have different shapes (e.g., flat aromatic rings(s), puckered aliphatic rings(s), straight and branched chain aliphatics with single, double, or triple bonds) and diverse functional groups (e.g., carboxylic acids, esters, ethers, amines, aldehydes, ketones, and various heterocyclic rings) for maximizing the possibility of discovering compounds that interact with widely diverse binding sites on the target effector molecule under consideration.

For the sake of brevity and clarity, the examples that follow are limited largely to an investigation into the rational design of ligands that bind to the Human Immunodeficiency Virus (HIV) transactivation response region RNA (HIV-TAR) using the methods provided in accordance with the present technology. The same methodology as described herein can be used to investigate any receptor-ligand, enzyme-substrate complex and nucleic acid-regulatory element activity, without limitation.

The TAR RNA element is positioned immediately after the transcription start site (nt+1 to +59) and forms a stable hairpin structure. Tat binds in the region of a three base (UCU or UUU) bulge and recognizes both the identity of adjacent Watson-Crick base pairs and the positions of surrounding phosphate groups. The interaction between Tat and TAR is essential for viral growth; mutants in TAR with reduced affinity for Tat are unable to replicate efficiently. HIV 1 and 2-TAR were chosen as an illustrative RNA target effector molecule for investigation because of their clinical importance in HIV since TAR binds a variety of proteins and is a target for developing anti-HIV therapies. Moreover, the structure of the HIV-1 TAR RNA has been determined (Aboul-ela, F. et al., Nucl. Acids Res. (1996); 24(20):3974-3981).

Embodiments

In one aspect, the invention provides a method for analyzing the structural conformations of a target effector molecule comprising:
  a. providing a target effector molecule having an artificial elongated sequence comprising one or more variable kinks;
  b. obtaining residual anisotropic interaction and spin relaxation data from said target effector molecule having said elongated structure using nuclear magnetic resonance spectroscopy, X-ray crystallography or both;
  c. creating a plurality of atomic-resolution dynamical ensembles reflecting motional trajectories of said target effector molecule by constructing computational models of said target effector molecule using computer modeling programs selected from:
    Molecular Dynamics, Monte Carlo, CHARMM, FELIX, QUANTA, and GrowMol, or combinations thereof;

d. selecting a plurality of said dynamical sub-ensembles using Monte Carlo simulation to generate a plurality of conformers that satisfy said residual anisotropic interactions and spin relaxation data obtained in step b;

e. identifying a plurality of dominant conformers from said dynamical ensembles; and f. selecting and outputting said dominant conformers and motional trajectories of said target effector molecule.

In one embodiment of this aspect, the target effector molecule is a polypeptide, a protein, a polysaccharide, a nucleic acid, a lipid, a glycoprotein, a glycolipid or a combination thereof.

In another embodiment, the target effector molecule is a polysaccharide, a nucleic acid, a lipid, a glycolipid or a combination thereof.

In another embodiment, the target effector molecule is a nucleic acid.

In a further embodiment, the target effector molecule is an RNA molecule having 2 to 1000 base pairs.

In one embodiment, the variable kink in step 'a' is a section of the target effector molecule which comprises a bulge, an internal loop or an n-way junction.

In another embodiment, the variable kinks vary from each other in at least one of sequence length, position of said kink in said target effector molecule or symmetry.

In another embodiment, the internal loop is asymmetric or symmetric.

In one embodiment, the computer modeling program used in step 'c' is MD.

In one embodiment, step 'b', above, is performed on a target effector molecule in the presence of a ligand, said ligand having affinity for the active site of said target effector molecule, and wherein the conformations of the target effector molecule reveal the binding portion of the target effector molecule to a putative ligand structure.

In a further embodiment, the method comprises screening a plurality of ligands to rank the binding strength of each of said ligands with the plurality of computational models selected, having a root-mean square deviation below a predetermined threshold.

In a further embodiment, the method comprises selecting one or more ligands based on their individual rank.

In another embodiment, the ligand is a small organic molecule, a peptide, a polynucleotide, a carbohydrate and polymers thereof.

In another aspect, the invention is a computer system configured to analyze the structural conformations of a target effector molecule by:

a. generating a plurality of conformers from a plurality of dynamical sub-ensembles obtained using Monte Carlo simulation that satisfy residual anisotropic interaction and spin relaxation data obtained from the target effector molecule, having an elongated structure, using nuclear magnetic resonance spectroscopy, X-ray crystallography or both;

b. identifying a plurality of dominant conformers from the dynamical ensembles; and c. selecting and outputting the dominant conformers and motional trajectories of the target effector molecule.

In one embodiment of this aspect, the target effector molecule is in the presence of a ligand, the ligand having affinity for the active site of the target effector molecule, and wherein the conformations of the target effector molecule reveal the binding portion of the target effector molecule to a putative ligand structure.

In another embodiment, the system is further designed to screen a plurality of ligands and rank the binding strength of each of the ligands with the plurality of computational models selected, having a root-mean square deviation below a predetermined threshold.

In another embodiment, the system is further designed to select one or more ligands based on their individual rank.

In another aspect, the invention provides a method for generating putative ligand structures capable of altering the activity of a target effector molecule, the method comprising:

(a) constructing an elongated monomer of the target effector molecule;

(b) constructing a three dimensional model of the target effector molecule under the influence of elongation using empirical three dimensional data, the model including a conformation revealing the binding portion of the target effector molecule to a putative ligand structure;

(c) generating a plurality of computational models of the target effector molecule;

(d) filtering the plurality of computational models against the three dimensional model created in step (b) using a reiterative simulation analysis algorithm operable to identify and select a plurality of computational models having a root-mean square deviation below a predetermined threshold when compared to the three dimensional model of the target effector molecule;

(e) screening a plurality of ligands to rank the binding strength of each ligand with the plurality of computational models selected having a root-mean square deviation below a predetermined threshold; and (f) selecting one or more ligands based on the ranking determined in step (e).

In one embodiment of this aspect, the target effector molecule is a polypeptide, a protein, a polysaccharide, a nucleic acid, a lipid, a glycoprotein, a glycolipid and combinations thereof.

In another embodiment, the empirical three dimensional data used in step (b) is X-ray crystallographic data.

In one embodiment, the empirical three dimensional data used in step (b) is nuclear magnetic resonance data.

In one embodiment, the empirical three dimensional data used in step (b) is X-ray crystallographic data and nuclear magnetic resonance data.

In another embodiment, the generating a plurality of computational models of the target effector molecule comprises constructing computational models using any one or more computer modeling programs comprising: Molecular Dynamics, Monte Carlo, CHARMM, FELIX, QUANTA and GrowMol.

In one embodiment, the generating a plurality of computational models of the target effector molecule comprises constructing computational models using Molecular Dynamics.

In one embodiment, the ligand is a small organic molecule, a peptide, a polynucleotide, a carbohydrate and polymers thereof.

In a further embodiment, the ligand is a species of a combinatorial library.

In another aspect, the present technology provides a method for analyzing the structural conformations of a target effector molecule that can be targeted with a small molecule, the method comprising:

a. providing a target effector molecule having an artificial elongated sequence having one or more variable kinks;

b. obtaining residual anisotropic interactions and spin relaxation data from the target effector molecule having the elongated structure;

c. creating a plurality of atomic-resolution dynamical ensembles reflecting motional trajectories of the target effector molecule;
d. selecting a plurality of the dynamical subensembles using Monte Carlo simulation to generate a plurality of conformers that satisfy the residual anisotropic interactions and spin relaxation data;
e. identifying a plurality of dominant conformers from the dynamical ensembles that can be targeted by a small molecule; and
f. selecting and outputting the dominant conformers and motional trajectories of the target effector molecule.

In one embodiment of this aspect, the target effector molecule is a polypeptide, a protein, a polysaccharide, a nucleic acid, a lipid, a glycoprotein, a glycolipid and combinations thereof.

In another embodiment, the target effector molecule is a biologically active fragment of the polypeptide, a protein, a polysaccharide, a nucleic acid, a lipid, a glycoprotein, a glycolipid.

In one embodiment, the variable kinks comprise one or more of a bulge, an internal loop, an n-way junction.

In a further embodiment, the variable kinks vary from each other in at least one of sequence length, position of kink in the target effector molecule and symmetry.

In a further embodiment, the internal loop is asymmetric or symmetric.

In one embodiment, the residual anisotropic interactions and spin relaxation data used in step (b) is X-ray crystallographic data.

In one embodiment, the spin relaxation data used in step (b) is nuclear magnetic resonance data.

In a further embodiment, the residual anisotropic interactions and spin relaxation data used in step (b) is X-ray crystallographic data and nuclear magnetic resonance data.

In one embodiment, creating a plurality of atomic-resolution dynamical ensembles comprises constructing computational models of the target effector molecule using any one or more computer modeling programs comprising: Molecular Dynamics, Monte Carlo, CHARMM, FELIX, QUANTA and GrowMol.

In one aspect, the invention provides an in vitro method of inhibiting or suppressing at least one of HIV-1 replication or KSHV replication in a host cell infected with HIV-1 or KSHV, comprising the step of administering to the host cell a compound capable of interfering with the binding of at least one C-X-C chemokine selected from the group consisting of IL-8, GCP-2, GRO-α, GRO-β, GRO-γ, IP-10, 1-TAC, MIG with its respective C-X-C chemokine receptor selected from the group consisting of CXCR1, CXCR2 and CXCR3 such that the receptor activity is diminished.

In one embodiment of this aspect, the compound is an antibody.

In another embodiment, the antibody binds to a C-X-C chemokine.

In a further embodiment, the antibody is anti-IL-8, anti-GRO-α or anti-IP-10.

In one embodiment, the antibody binds to a C-X-C chemokine receptor.

In a further embodiment, the antibody is anti-CXCR1, anti-CXCR2, or anti-CXCR3.

In one embodiment, the compound is a small molecule inhibitor.

In a further embodiment, the small molecule inhibitor is SB225002.

In one embodiment, the compound is a peptide.

In a further embodiment, the peptide is antileukinate.

In another aspect, the invention is a medicament comprising a compound capable of interfering with the binding of at least one C-X-C chemokine selected from the group consisting of IL-8, GCP-2, GRO-α, GRO-β, GRO-γ, IP-10, 1-TAC, MIG with its respective C-X-C chemokine receptor selected from the group consisting of CXCR1, CXCR2 and CXCR3 such that the receptor activity is diminished, for the treatment of HIV-1 infection, KSHV infection, AIDS or Kaposi's sarcoma.

In one embodiment of this aspect, the compound is an antibody.

In a further embodiment, the antibody binds to a C-X-C chemokine.

In one embodiment, the antibody is anti-IL-8, anti-GRO-α, or anti-IP-10.

In another embodiment, the antibody binds to a C-X-C chemokine receptor.

In a further embodiment, the antibody is anti-CXCR1, anti-CXCR2, or anti-CXCR3.

In one embodiment, the compound in a small molecule inhibitor.

In a further embodiment, the small molecule inhibitor is SB225002.

In one embodiment, the compound is a peptide.

In a further embodiment, the peptide is antileukinate.

In another aspect, the invention provides an in vitro method of inhibiting or suppressing at least one of HIV-1 replication or KSHV replication in a host cell infected with HIV-1 or KSHV, comprising the step of administering to the host cell a compound capable of inhibiting or suppressing expression of at least one C-X-C chemokine receptor selected from the group consisting of CXCR1, CXCR2 and CXCR3.

In one embodiment of this aspect, the compound is an antisense nucleic acid molecule.

In another embodiment, the compound is a vector comprising a gene encoding dominant mutant inactive form of the C-X-C chemokine receptor.

In another aspect, the invention is a medicament comprising a compound capable of inhibiting or suppressing expression of at least one C-X-C chemokine selected from the group consisting of IL-8, GCP-2, GRO-α, GRO-β, GRO-γ, IP-10, 1-TAC, MIG for the treatment of HIV-1 infection, KSHV infection, AIDS or Kaposi's sarcoma.

In one embodiment of this aspect, the compound is an antisense nucleic acid molecule.

In another embodiment, the compound is a vector comprising a gene encoding for a dominant mutant inactive form of the C-X-C chemokine.

In another aspect, the invention is a medicament comprising a compound capable of inhibiting or suppressing expression of at least one C-X-C chemokine receptor selected from the group consisting of CXCR1, CXCR2 and CXCR3 for the treatment of HIV-1 infection, KSHV infection, AIDS or Kaposi's sarcoma.

In one embodiment of this aspect, the compound is an antisense nucleic acid molecule.

In another embodiment, the compound is a vector comprising a gene encoding for a dominant mutant inactive form of the C-X-C chemokine receptors.

In another aspect, the present disclosure includes a processor, including a microprocessor, configured to perform the method described in any one of claim 1-14 or 19-37. In some embodiments a computer memory includes instructions stored in memory to execute or perform at least some of the computer modelling and/or computer simulation algorithms.

In another aspect, the present disclosure includes a computer configured to perform the method described in any of claim 1-14 or 19-37.

In another embodiment, a computer readable medium having embedded therein computer executable instructions for analyzing the structural conformations of a target effector molecule that can be targeted with a small molecule, the computer readable medium comprising a process A, embodied as computer executable instructions of inputting residual anisotropic interaction and spin relaxation data obtained from a target effector molecule having an elongated sequence, said sequence having one or more variable kinks;

a process B, embodied as computer executable instructions of (i) creating a plurality of atomic-resolution dynamical ensembles reflecting motional trajectories of the target effector molecule;

(ii) selecting a plurality of the dynamical subensembles using Monte Carlo simulation to generate a plurality of conformers that satisfy the residual anisotropic interactions and spin relaxation data;

(iii) identifying a plurality of dominant conformers from the dynamical ensembles that can be targeted by a small molecule; and (iv) selecting and outputting the dominant conformers and motional trajectories of the target effector molecule.

In one embodiment, the target effector molecule can be in a modified form, relative to the wild-type molecule.

In one embodiment, the target effector molecule can be modified by elongation.

In a further embodiment, the target effector molecule is an RNA molecule and the elongation can be accomplished by adding base pairs onto the length of the RNA molecule.

In a further embodiment, the elongation is done in a fashion that will not effect the biological activity of the target effector molecule.

In another further embodiment, the elongation is done in a fashion that will not significantly effect the biological activity of the target effector molecule.

In another further embodiment, the target effector molecule retains at least 90% biological activity after elongation, as compared to the unmodified target effector molecule.

In one embodiment, the target molecule can be modified by adding a variable kink.

In a further embodiment, the target effector molecule is an RNA molecule and the variable kink is a bulge.

In another further embodiment, the target effector molecule is an RNA molecule and the variable kink is an internal loop.

In another further embodiment, the target effector molecule is an RNA molecule and the variable kink is an n-way junction.

High Throughput Ensemble-Based Docking Against Flexible Biomolecular Targets

A generalized approach to identify a putative binding ligand with a target effector molecule is depicted in the claims. Initially, the target effector molecule is elongated using the same kind of building blocks used in the synthesis of the target effector molecule. In the example of RNA, the elongation step of the target effector molecule can be made by adding specific ribonucleotides to the ribonucleotide sequence of the target effector molecule. These added ribonucleotide sequences can include AU rich sequences, CG rich sequences and mixtures thereof. In some embodiments, studying the helical structure of a target effector molecule can be further improved by adding building blocks to the sequence that creates a three dimensional perturbation to the structure distal to the putative ligand binding site of the target effector molecule. The net effect of adding or elongating the sequence of the target effector molecule is to make overall motions of the effector molecule insensitive to internal motions within the target effector molecule active site. Q. Zhang, X. Sun, E. D. Watt et al., *Science* 311 (5761), 653 (2006). The elongation can consist of any biologically inert material and generally consists of any nucleic acid sequence that forms an elongated structure.

Once the target effector molecule has been elongated, the elongated target effector molecule is analyzed and measured using an empirical three dimensional analysis technique. Suitable techniques for measuring the physicochemical structure of the target effector molecule can include X-ray crystallography, and Nuclear Magnetic Resonance (NMR) techniques. Methods for studying the HIV-1 & HIV-2 Transactivation Response Elements (TAR) using NMR have been described in Dethoff, E. A., et al., (2008), Biophys. J. and in RNA in general: Zhang, Q., and Al-Hashimi, H. M.*, Extending the NMR Spatial Resolution Limit in RNA by Motional Couplings. Nat. Methods 5(3):243-5 2008 and Zhang, Q., et al., (2007), Nature, 450:1263-7, whose disclosures are hereby incorporated herein in their entireties.

A preferred NMR-based technique for evaluating the relative orientations of target effector molecules depends upon the observation and interpretation of dipolar coupling within the individual target effector molecules when the ligands are simulated under various temperatures and binding conformations. By generating a field ordered state of the first and second target effector molecule conformation (for example, bound and unbound), one can acquire NMR spectra from which dipolar couplings within the target effector molecule can be analyzed and determined, and from which the spatial orientation of dipole-dipole interactions can be deduced. With knowledge of the spatial orientation of the dipole-dipole interactions, one is then able to model the spatial orientation of the atoms within the target effector molecule. The present technology is not limited to NMR methods for determining spatial orientation of the atoms of the target effector molecule, and other known methods such as X-ray crystallography can be employed instead.

Once the physical measurement of the target effector molecule has been completed, sampling of the conformational space of the target effector molecule can commence. In some embodiments, the sampling can be performed with any known molecular modeling computational program known in the art. A host of such programs are available commercially and are suitable for use in the present invention. The programs can be stored on a suitably programmed computer and/or on computer or microprocessor memory.

In some embodiments, any one or combination of computer molecular modeling programs can be used in the methods of the present technology. These can include for example, a program called “GrowMol.” The program itself is described in great detail in Bohacek & McMartin (1992) J. Med. Chem. 35(10):1671-1684; Bohacek & McMartin (1994) J. Am. Chem. Soc. 116:5560-5571; Bohacek & McMartin (1995) SIAM J. Math Anal. 116:147-179; Bohacek, McMartin, & Guida (1996) Med. Res. Rev. 16(1):3-50; Rich, Bohacek, Dales, Glunz & Ripka (1996) in Actualites de chimie therapeutic, Elsevier: Amsterdam 101-111; and Ripka & Rich (1998) Curr. Op. in Chem. Biol. 2:441-452.

The program can be obtained from a number of university sources, including from the University of Wisconsin-Madison. The program can also be obtained directly from its principal author, Regine Bohacek of Boston De Novo Design, Boston, Mass. The "GrowMol" program is capable of generating organic structures that are both spatially and chemically complementary to a mathematically-defined receptor binding site. The program mathematically constructs molecules, one atom at a time, to occupy the mathematically-defined space of a binding site. In this fashion, the "GrowMol" program can be used to generate chemical structures whose physical and chemical properties are complementary to the receptor binding site. At each reiteration of the construction process, the position and type of atom to be added to the model are randomly selected using Boltzmann statistics, in an effort to bias acceptance toward atoms that can form favorable interactions with the binding site.

Another computer program that is very useful in conjunction with the "GrowMol" program is called "Flo." The "Flo" program is a molecular modeling program written by Colin McMartin. The program aids in visualizing molecules and in designing lead drug compounds. The "Flo" program is available online at uwmml.pharmacy.wisc.edu/Flo/floindx.html. The "Flo" program is also marketed commercially through Thistlesoft Software Co., Morris Town, N.J. The "Flo" program can also be obtained directly from its author, Colin McMartin, at cmcma@ix.netcom.com. The great advantage of using the "Flo" program in conjunction with the "GrowMol" program is that the "Flo" program provides a front-end graphical interface that enables molecular models to be formatted more easily for analysis using the "GrowMol" program.

Other equally suitable chemical modeling programs are available commercially or through academic outlets. For example, Tripos of St. Louis, Mo., markets a very wide range of molecular modeling and analysis programs, including the "Advanced Computation," "AMPAC," "CONFORT," "MM3 (2000)," "MOLCAD," and "SYBYL/Base" programs.

Briefly, the "Advanced Computation" program provides a wide range of tools for conformational analysis, including calculations that enumerate all possible torsional states of a molecule or identify just its low-energy conformations.

The "AMPAC" program calculates structures and electronic properties of molecules using semi-empirical quantum mechanical methods.

The "CONFORT" program performs conformational analyses of drug-sized molecules to identify the global minimum energy conformer, all local minima within a user-specified energy range, or a maximally diverse subset of conformers.

The "MM3 (2000)" program is a molecular mechanics program that produces high-quality three-dimensional structures and computes molecular energy, vibrational spectra, and a variety of thermodynamic and spectroscopic quantities.

The "MOLCAD" program creates and displays molecule surfaces onto which it maps key properties, including lipophilicity, electrostatic potential, hydrogen bonding sites, and local curvature.

The SYBYL/Base program includes a comprehensive suite of sub-programs for molecular modeling, including structure building, optimization, and comparison; visualization of structures and associated data; annotation, hardcopy and screen capture capabilities; and a wide range of force fields.

Accelrys Inc. (San Diego, Calif.), a subsidiary of Pharmacopeia Inc., is another commercial supplier of suitable molecular modeling software for use in the present technology. As noted above, the present technology requires three-dimensional data on the target effector molecule. Accelrys' "QUANTA" program can be used for processing of X-ray data, electron density fitting, and model building; the "CNX" program can be used for phasing and refining of the initial X-ray model. If NMR data is available for the target effector molecule, Accelrys' "FELIX" and "Insight II" NMR modules can be used for spectral data processing, and for refining and evaluating putative structures and conformations. Accelrys also markets a line of "Insight II" modules, including the "MODELER," "Biopolymer," "Homology," "SeqFold," and "Binding Site Analysis" modules. These programs can be used to model and to predict the conformational space and structure of protein target effector molecules.

As noted above, macromolecules are not static structures. They move, vibrate, and interact with other molecules and their environment. Understanding these movements and interactions is essential for constructing an accurate model of the target effector molecule. Molecular modeling step contemplates the computational simulation of the target effector molecule rendering snapshots or computational models of the target effector molecule over a period of time and under different conditions of temperature, solvation and binding states. In some embodiments, Accelrys markets a program, "CHARMm," for dynamic modeling of macromolecules which is a preferred program for use in the present technology with relation to nucleic acid target effector molecules. The "Insight II" program also includes modules capable of dynamic molecular modeling, including the "Discover," and "Decipher" modules. The "QUANTA" program is also capable of dynamic modeling. Yet another Accerlrys program, "Cerius2" enables dynamic modeling, especially when using the "Cerious2" modules "C2.OFF" and "C2.CFF."

Taken together, these programs from Accelrys enable model building of small molecules and biomolecules, graphical model manipulation, energy minimization, graphical trajectory display, and data analysis.

A number of other companies, as well as academicians, have also released molecular modeling programs that can be used in the present invention. A great many of these programs can be obtained through IBM's High Performance Computing Division, Armonk, N.Y. A non-exhaustive list of suitable programs available through IBM and the names of the original suppliers includes the following: Supplier Name Program(s) CCP4 Consortium CCP4 SQ University of Vienna VASP/VAMP Univ of Cal. at San Francisco AMBER 6 SemiChem AMPAC CAChe (Fujitsu) CONFLEX Extended Huckel MD Tabulator ZINDO MOPAC Molecular Mechanics Iowa State University GAMESS Gaussian Inc. Gaussian 98 Schrodinger Jaguar MOPAC2000 Macromodel University of Birmingham MOLPRO **Pacific Northwest National Lab NWChem Accelrys (see above) OFF Dynamics OFF Minimize Discover DMOL CHARMM DGAUSS Polymorph Predictor Qchem QChem University of Minnesota AMSOL 6.6 University of Ottawa DEFT Thistlesoft FLO/QXP Another program that can be utilized in the methods of the present technology is called DEZYMER, developed by Homme Helling a of Duke University. See Helling a & Richards (1991) J. Mol. Biol. 222:763-785; and Hellinga, Caradonna, & Richards (1991) J. Mol. Biol. 222:787-803.

In some embodiments, the modeling of the computational snapshot or computational models of the target effector molecule under various conditions can be performed using MD. MD is a form of computer simulation in which atoms and molecules are allowed to interact for a period of time by approximations of known physics, giving a view of the motion of the atoms. MD theory and applications have been discussed in B. J. Alder and T. E. Wainwright, J. Chem. Phys. (1957) 1208; D. Chandler, "Introduction to Modern Statistical Mechanics", (1987, Oxford University Press); M. J. Gillan, Phys. Scripta, 362 (1991). P. J. D. Lindan and M. J. Gillan, J. Phys.: Condens. Matter 3, 3929 (1991); M. P. Allen and D. J. Tildesley, "Computer Simulation of Liquids", (Oxford University Press, 1987) and J. M. Haile, "Molecular dynamics simulation: elementary methods", (Wiley, 1992).

In some embodiments, the modeling and derivation of the computational snapshot or computational models of the target effector molecule under various conditions can also be performed using MC methods. Numerical methods known as MC methods can be loosely described as statistical simulation methods, where statistical simulation is defined in general terms to be any method that utilizes sequences of random numbers to perform the simulation. MC methods have been used for centuries, but only in the past several decades has the technique gained the status of a full-fledged numerical method capable of addressing the most complex applications. MC is now used routinely in many diverse fields, from the simulation of complex biological phenomena and the simulation of sub-nuclear processes in high-energy physics experiments, to the mundane, such as the simulation of a Bingo game. The analogy of MC methods to games of chance is quite apt, but the "game" to be analyzed here is the plausible conformations of the binding site of a target effector molecule, and the outcome of the game is not a pot of money, but rather a solution to the problem of determining the shape of a binding ligand that will bind to one or more of the plausible conformations of the binding site.

Statistical simulation methods such as MC can be contrasted to conventional numerical discretization methods, which typically are applied to ordinary or partial differential equations that describe some underlying physical or mathematical system. In most applications of MC, the physical process is simulated directly, and there is no need even to write down the differential equations that describe the behavior of the system. The only requirement is that the physical system, in this case, the receptor-ligand complex, be described by probability density functions (pdf s). Insofar as X-ray crystallographic data yields an electron density map or NMR yields residual spin coupling data, these data are very well suited for analysis via MC methods. Once the pdfs are known, the MC simulation can proceed by random sampling from the pdfs. Many simulations are then performed reiteratively (multiple "trials" or "histories") and the desired result is taken as an average over the number of observations (which may be a single observation or perhaps millions or billions of observations).

Regardless of the system being modeled, every MC approach shares certain major components. A full discussion of these components, as well as the physical and mathematical underpinnings of the same, is available in the published literature and accessible to one of ordinary skill in the art. A good starting point is "Introduction to MC Methods", (1996), Computational Science Foundation Project, Verena Meiser, Ed. (Vanderbilt University, Nashville, Tenn.) (sponsored by the U.S. Department of Energy).

The primary components of a MC simulation method include the following: (i) a set of probability distribution functions (pdfs): the physical system, i.e., the geometry and chemistry of the target effector molecule-ligand complex, is described by a set of pdfs; (ii) a random number generator: a source of random numbers uniformly distributed on the unit interval must be available; (iii) a sampling rule: a prescription for sampling from the specified pdfs, assuming the availability of random numbers on the unit interval, must be given; (iv) scoring (or tallying): the outcomes must be accumulated into overall tallies or scores for the quantities of interest (bond lengths, angles, rotation, steric interactions, etc.); (v) error estimation: an estimate of the statistical error (variance) as a function of the number of trials and other quantities must be determined; (vi) variance reduction techniques: methods for reducing the variance in the estimated solution to reduce the computational time for MC simulation; and (vii) parallelization and vectorization: algorithms to allow MC methods to be implemented efficiently on advanced computer architectures.

Using these foundational elements, the plausible conformations of a target effector molecule binding, active or regulatory site can be modeled and analyzed via a MC approach that is implemented on a suitably programmable computer, or microprocessor.

Once the computational models depicting various snapshots of the target effector molecule under various conditions (otherwise known as conformers) are obtained, the filtering of the plurality of computational models or snapshots against the three dimensional experimental data obtained of the target effector molecule can be achieved. This step takes the pool of conformers which can range from 10 to $1 \times 10^6$ computational models derived from MD or MC computations and then searches for a subset population of computational models that minimizes the cost function. To calculate the minimized cost function, specific RDC average values for a given conformation structure ensemble can be compared with an experimentally derived RDC measures along a specific structure of the target effector molecule. In some embodiments, the filtering can be achieved using a MC simulated annealing algorithm to minimize the cost function. During each constant temperature cycle of MC simulated annealing, random changes are made to the ligand's current position, orientation, and conformation, if flexible. The new state is then compared to its predecessor. If its new energy is lower than the previous, this new state is immediately accepted. However, if the new state's energy is higher than the last, it is accepted probabilistically. This probability depends upon the energy and cycle temperature. Generally speaking, at high temperatures, many states will be accepted, while at low temperatures, the majority of these probabilistic moves will be rejected. The computational model, or snapshot, is filtered by accepting or rejecting the computational model based on the standard Metropolis criterion. (Metropolis, N. et al. (1953). J. Chem. Phys. 21:1087-1092). The use of MC simulation with the Metropolis criterion can be applied to any ensemble of molecules. In essence using the Metropolis criterion is a % deviation from the RDC average measured in solution. Reference describing the SAS method but applied in a different context (Chen Y. et al. (2007). Biophys. Journal. 93:2300-2306).

The next step requires the analysis of the plurality of computational models obtained above, that have passed a specific threshold. These snapshots or computational models generally represent N conformers that recapitulate the target effector molecule internal dynamics. In some embodiments the root-mean square deviation between the computed and measured RDCs can be used as a basis for selecting the conformers that are to be screened virtually using a plurality of ligands. This part of the method is a virtual screening process that enables the elimination of conformers or computational models that do not truly reflect the internal dynamics of the target effector molecule and thus corrupts the ligand identification process.

In some embodiments, the virtual screening in effect measures the ability of one ligand to bind to all of the selected computation models identified above. A binding result for each ligand computationally measured enables a reiterative approach to virtually screen thousands, hundreds of thousands and even millions of compounds rapidly. The binding computations to each snapshot can be performed using any previously known docking program. Selection of the ligand may be influenced by certain physiochemical characteristics that may be unique to the target effector molecule tested. For example, in the case of RNA target effector molecules, ligands that have an nFLEX number below a certain predetermined threshold are used to virtually screen the selected conformers or computational models. Other parameters such as protonation of the ligand may be altered in order to achieve a meaningful virtual screening result. In order to account for all small molecule microspecies potentially existing in solution as well as local protonation changes that potentially occur upon binding, all protonation states at pH values of 5.4 to 9.4 are used in docking simulations. Molecular weight (<600 Da), number of hydrogen bond donors (<25), and number of nitrogen atoms and oxygen atoms (<20) are also specified in the simulations. Further, potential binding sites are identified on the effector molecules prior to simulations so as to rapidly identify good scores and accurate binding poses without wasting search time searching in areas of the effector molecule that will likely not effectively bind a small molecule.

Docking programs for a variety of target effector molecules can be used, for example the ICM program and ICM Docking and chemistry module from Molsoft LLC, (La Jolla, Calif., USA). Ligands that have the highest average binding coefficients for the plurality of selected computation models or snapshots identified above can then be ranked accordingly. Each putative ligand can undergo further experimentation as lead compounds that are capable of affecting the activity of the target effector molecule.

Experimental validation can be accomplished using any established structure activity assay using the identified ranked ligands in competition assays, functional assays and binding assays. All of these experimental validation assays can be performed using high-throughput methodologies.

Modulating Nucleic Acid Alignment by Kinked Helix Elongation-Characterization of Nucleic Acid Motions with Maximum Spatial Resolution Methods for Producing Target Effector Molecule Conformers with Maximum Resolution for High Throughput Structure Determination The present technology provides for enhancements in the determination and calculation of the target effector molecule or target effector sequence structure and more importantly, the motional trajectories or paths of the target effector molecule or target effector sequence structure when bound to a ligand with maximum spatial resolution. The present technology overcomes the problems associated with experimentally accessing the five independent alignment conditions needed to characterize motions in complex biological molecules, for example, nucleic acids with maximum spatial resolution.

In one embodiment, a method for characterizing the motions in nucleic acids with maximum spatial resolution can be achieved by accessing five independent motionally decoupled alignments in the examined nucleic acid(s). The method includes introducing variable kinks in the elongated nucleic acid helices. The variable kinks have specific structural and dynamical properties and are positioned in the nucleic acid sequence of the examined nucleic acid at positions for modulating overall alignment. As used herein, a kink can include any structural motif that interrupts the double helix, including bulges, internal loops, and n-way junctions. The required deviations from axial symmetry is accomplished by introducing kinks that give rise to asymmetric internal helix motions such as the motions observed for the nucleic acid under examination.

The present technology also provides for methods for increasing NMR data (i.e. increased residual dipolar coupling) density by modulating RNA alignment using kinked-helix elongation. The RDC density can be increased significantly by changing the overall alignment of the RNA and measuring distinct RDC data sets that report different stereoviews of the bond vector orientation relative to the alignment frame. A theoretical maximum of five such independent sets of RDCs can be measured under five linearly independent alignment conditions. The five sets of RDCs measured per bond vector makes it possible to extract all five motionally averaged Wigner rotation elements, $\langle D_{0i}^2(\alpha,\beta)\rangle$ describing the orientational distribution of the axially symmetric dipolar vector, where α and β are polar angles defining the orientation of the bond vector relative to the principal axis system (PAS) of the overall alignment frame.

The measurement of five independent RDC sets in RNA and nucleic acids in general has proven to be an intractable problem. Though it has been shown that five independent alignments can be accessed for proteins by simply changing the alignment medium and altering the balance of electrostatic and steric forces governing solute alignment, this proves to be impossible for nucleic acid target effector molecules, for example, RNA likely because the uniform electrostatic charge distribution closely follows that of the steric molecular shape. Spontaneous magnetic field alignment can yield one additional independent alignment, but the degree of alignment is often unfavorably small. The problem of modulating RNA alignment grows in its complexity when also imposing the requirement of keeping internal motions decoupled from overall reorientation.

In some embodiments, methods for generating putative ligand structures capable of altering the activity of a target effector molecule have used studies of TAR which have so far relied on two sets of motionally decoupled RDC sets measured on two elongated RNA sampled in which each of TAR's two helices are independently elongated.

In some embodiments, the methods disclosed herein can be used for accessing up to five independent motionally decoupled RDC data sets for a target effector molecule, for example, RNA. The method includes installing variable dynamic kinks to the elongated terminal helix. Illustrative models to show the effects of such kinked sequences are demonstrated and characterized using HIV-1 and HIV-2 TAR to predictably install dynamic deviations in the domain elongation. Without wishing to be bound by theory, it is believed that a kink in the nucleotide sequence causes the elongated nucleic acid helix to reorient relative to the reference terminal helix thus inducing a motionally averaged alignment for this helix that deviates from that observed for a static linear elongation.

Synthesis of the Kinked Target Effector Molecules

The variable amino acid and nucleic acid kinks can include specific linear synthesized amino acid or nucleic acids sequences that can be coupled to any sequence length of primary sequence from the target effector molecule that is the subject of analysis. As used herein, the term "nucleic acid molecule" can include DNA molecules and RNA molecules and analogs of the DNA or RNA molecule generated using nucleotide analogs. A nucleic acid molecule of the invention can be single-stranded or double-stranded, and the strandedness will depend upon its intended use. Nucleic acids include any nucleic acid molecule, including but not limited to, DNA or RNA. A DNA nucleoside is one of the four DNA bases covalently attached to the C1' position of a sugar. The sugar in deoxynucleosides is 2'-deoxyribose. The sugar in ribonucleosides is ribose. The deoxyribose sugar of the DNA backbone has 5 carbons and 3 oxygens. The carbon atoms are numbered 1', 2', 3', 4', and 5' to distinguish from the numbering of the atoms of the purine and pyrmidine rings. The hydroxyl groups on the 5'- and 3'-carbons link to the phosphate groups to form the DNA backbone. Deoxyribose lacks an hydroxyl group at the 2'-position when compared to ribose, the sugar component of RNA. Nucleosides differ from nucleotides in that they lack phosphate groups. The four different nucleosides of DNA are deoxyadenosine (dA), deoxyguanosine (dG), deoxycytosine (dC), and (deoxy)thymidine (dT, or T). A nucleotide is a nucleoside with one or more phosphate groups covalently attached to the 3'- and/or 5'-hydroxyl group(s).

RNA nucleotides include RNA molecules which are synthesized from three basic components: ribose, a five-carbon suger, phosphate, and a family of four heterocyclic bases. The backbone of RNA is an alternating polymer of ribose and phosphate wherein phosphodiester moeities bridge the O3' and O5' atoms from consecutive riboses. one of four heterocyclic bases is attached to the C1' atom of each ribose via a glycosidic linkage. These heterocycles are either purine derivatives (guanine and andenine) or pyrimidine derivatives (cytidine and uracil). Thymine, a pyrimidine normally found in DNA, is also occasionally used in RNAs. Furthermore, a large variety of base modifications are also observed in naturally occurring RNA molecules. The term nucleotide sequence encompasses sequences that include any of the known base analogs of DNA and RNA including, but not limited to, 4-acetylcytosine, 8-hydroxy-N-6-methyladenosine, aziridinylcytosine, psudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, 2,6-diaminopurine and combinations thereof. Other modified ribonucleobases useful in the present technology are commercially available from Glen Research, Sterling Va., USA.

Methods for Introducing a Kink to a Target Effector Molecule

Kinks can be synthesized using common nucleic acid synthesizers by specifically designating a primary sequence of a target effector molecule having one or more target effector sequences attached to a linker or non-coding sequence having one or more kinks. The kink can range from about 2 to about 500 nucleotides, more preferably from about 2 to about 100 nucleotides, or from about 2 to about 50 nucleotides, or from about 2 to about 25 nucleotides or still more preferably from about 2 to about 15 nucleotides.

A kink for example in a nucleic acid can include a bulge, an internal loop, and an n-way junction. A bulge can be used to induce an average bend causing the principal axis of alignment to no longer be parallel to the axis of the reference helix. Second, due to the asymmetry of the inter-helix motions induced by the bulge, the motionally averaged alignment tensor will deviate form axial symmetry.

The main assumption in subsequent data analysis is that the internal motions about the installed bulge do not affect or are not correlated to internal motions in other regions of the RNA target effector molecule. Thus, the Wigner elements describing the dynamics of bond vectors relative to the reference helix I $\langle D_{ij}^2(1 \rightarrow i) \rangle$ are unaffected by installation of the kinked elongated helix. Given the remote position of the installed bulge, it is expected that little to no correlations with internal motions within TAR and can be verified by comparing the NMR spectra of kinked-elongated TAR with those of linear-elongated TAR. In this manner, the SAS analysis can proceed in a straightforward manner, in which the new motionally averaged alignment tensor measured for the reference helix I is used in computing the RDCs.

In some embodiments, the number of kinked sequences adjacent or near a target effector sequence can vary over a given elongated primary sequence of nucleic acid or amino acid molecules. In addition to the installed trinucleotide bulge as shown illustratively in TAR, two additional kinks that serve to further modulate the alignment of the RNA can be inserted.

The kinked sequence can be placed anywhere along the nucleotide or amino acid primary sequence or elongated sequence which enables the elongated sequence to reorient relative to the reference primary sequence of the target effector molecule. The kink can be introduced into the target effector molecule using commonly used synthetic or recombinant techniques known in the art to produce a target effector molecule having a predetermined secondary structure based on its primary sequence. The method steps for preparing kinks in the target effector molecule can include phase-shifting the bulge by moving it one base-pair towards the 5' end of the RNA. Changes in the position of the kinks along the elongated linker sequence or primary sequence is expected to change the orientation of the $S_{zz}$ direction by a corresponding 33 degrees assuming 33 degree rotational twist per base-pair. Second, the length of the bulge will be reduced from three to two nucleotides. Based on studies of the HIV-2 TAR, which contains a dinucleotide bulge, it is expected that this will alter both the orientation as well as the asymmetry of the resulting alignment. The effects of altering the trinucleotide bulge asymmetry by using a 3-1 bulge. In an RNA structure in the PDB, is expected to induce ~33 degree rotational twist while also altering the asymmetry of alignment.

For the sake of brevity and clarity, the examples that follow are exemplified using an investigation into the rational design of ligands that bind to the Human Immunodeficiency Virus (HIV) transactivation response region RNA (HIV-TAR) using the methods provided in accordance with the present technology. The same methodology as described herein can be used to investigate any receptor-ligand, enzyme-substrate complex and nucleic acid-regulatory element activity, without limitation. The TAR RNA element is positioned immediately after the transcription start site (nt+1 to +59) and forms a stable hairpin structure. Tat binds in the region of a three base (UCU or UUU) bulge and recognizes both the identity of adjacent Watson-Crick base pairs and the positions of surrounding phosphate groups. The interaction between Tat and TAR is essential for viral growth; mutants in TAR with reduced affinity for Tat are unable to replicate efficiently. HIV 1 and 2-TAR were chosen as an illustrative RNA target effector molecule for investigation because of their clinical importance in HIV since TAR binds a variety of proteins and is a target for developing anti-HIV therapies. Moreover, the structure of the HIV-1 TAR RNA has been determined.

The method for characterizing the motions in nucleic acids with maximum spatial resolution relies on introducing variable kinks in a artificial elongated sequence which have strategically chosen structural and dynamical properties and positions for modulating overall alignment. The kink can be any structural motif comprising from about one to twenty five nucleotides or amino acids that interrupts the double helix. The variable kinks in the primary sequence of the target effector molecule can include bulges, internal loops, and n-way junctions. The required deviations from axial symmetry is accomplished by introducing kinks that give rise to asymmetric internal helix motions such as the motions observed for TAR RNA. Deviations from axial symmetry can also be accomplished by introducing three-way or high order junctions. The approach is demonstrated on the upper stem-loop of wild-type TAR RNA. Other methods to alter the alignment of the axis of the target effector molecule can include moving the kink in a 5' or 3' fashion (in amino acid sequences this would entail moving the kinking amino acids to the $NH_2$ terminus or the COO— terminus), by changing the length of the artificial elongated sequence, kink or linker sequence, changing the symmetry of the kink, i.e. as in the case of nucleic acids, one can change the number of residues on a first strand and have a higher or lower number of residues on the opposing strand. For example, the bulge in TARm created by the UCU sequence, which does not have any complementary nucleotides (match or mismatch) on the opposing strand.

As used herein, changing the nature of the kink as described above will alter the alignment of the target effector molecule in a magnetic field. Such changes enable altered alignments to be studied and characterized. Due to the asymmetry of the target effector sequence, for example in the case of nucleic acids, asymmetry of the inter helix motions induced by the kink, the motionally averaged tensor will deviate from axial symmetry. One can alter the 5 parameters of alignment in order to obtain the highest resolution of the various structural conformers possible for a given target effector molecule.

TABLE 1

Exemplary kinked nucleotide sequences for introducing kinks in RNA nucleic acid structures.

| Kink Nucleic No. | Nucleotide Sequence Of An RNA Target Effector Sequence Kink | SEQ ID NO: |
|---|---|---|
| 1 | UCUGAGCUUCGGCUC | 1 |
| 2 | GGACU****UCUGAGCUUCGGCUC | 2 |
| 3 | GG[YX]$_{10}$****UCUGAGCUUCGGCUC***[YX[$_{10}$CC | 3 |
| 4 | UCUGAG[YX]$_{10}$GCUUCGGC[YX]$_{10}$GCUC | 4 |
| 5 | GG[YX]$_{10}$****UUGAGCUUCGGCUC****[YX]$_{10}$CC | 5 |
| 6 | GGCAGAUCUGA********UCUCUGCC | 6 |
| 7 | GGACUCAGAUCUGA********UCUCUGAGUCC | 7 |
| 8 | GG[YX]10GGCAGAUCUGA********UCUCUGCC[YX]$_{10}$CC | 8 |
| 9 | GGCAGAUCUGAGC[YX]$_{10}$********[YX]$_{10}$GCUCUCUGCC | 9 |
| 10 | GG[YX]$_{10}$GGCAGAUUGA********UCUCUGCC[YX]$_{10}$CC | 10 |

*denotes a nucleotide of the of the target effector molecule being examined.
[YX] denotes random nucleotides selected from A, T, C, G, and U.

Calculation of the Five Distinct Alignments for Every Inter-Helical Junction

Methods for analyzing the structural conformations of a target effector molecule that can be targeted with a small molecule are described herein. In such methods, the structural conformations of the target effector molecule (an RNA, DNA or polypeptide molecule) can be captured in an ensemble or movie that provides maximum resolution. The structural conformation of the target effector molecule having an elongated and kinked structure can have a maximum resolution because until the present disclosure it was not known how to decouple.

In some embodiments a method for analyzing the structural conformations of a target effector molecule that can be targeted with a small molecule comprises: a. providing a target effector molecule having an artificial elongated sequence having one or more variable kinks; b. obtaining residual anisotropic interactions and spin relaxation data from the target effector molecule having the elongated structure; c. creating a plurality of atomic-resolution dynamical ensembles reflecting motional trajectories of the target effector molecule; d. selecting a plurality of the dynamical subensembles using Monte Carlo simulation to generate a plurality of conformers that satisfy the residual anisotropic interactions and spin relaxation data; e. identifying a plurality of dominant conformers from the dynamical ensembles that can be targeted by a small molecule; and f. selecting and outputting the dominant conformers and motional trajectories of the target effector molecule.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

EXAMPLES

Example 1

Method for Analyzing the Structural Conformations Of RNA Nucleic Acid Molecule HIV-TAR. (See also, Al-Hashimi, H. M., et al.; *Nucleic Acids Res.*, 2009, 37(11), 3670-3679; the contents of which are herein incorporated by reference in its entirety.)

Simulations of wild-type HIV-1 and HIV-2 TAR were performed using the CHARMM package with force field parameter set 27. Model 3 of the unbound NMR structure of HIV-1 TAR (PDB 1ANR) was used as starting coordinates for simulations of HIV-1 TAR. For 60 HIV-2 TAR, starting coordinates were obtained by removing argininamide from model 1 of the argininamide-TAR NMR structure (PDB 1AKX). The RNA was charge-neutralized using sodium counter ions and solvated in a 33-35 Å sphere of TIP3 water. A spherical boundary potential was applied to maintain the density of water around the RNA site. The system was minimized and heated to 300 K, while harmonically constraining the heavy atoms of the RNA with a force constant of 62 kcal/mol/A° for 100 ps, after which constraints were removed and the system equilibrated for 1 ns. A Nosé—Hoover thermostat was used to maintain a constant temperature of 300K throughout the simulation, with a 1 femtosecond (fs) time-step and a coupling constant of 50 $ps^{-1}$. Fifty distinct trajectories were initiated from this equilibrated structure, by assigning different initial velocities. It has previously been demonstrated that this technique can be used to enhance conformational sampling relative to a single trajectory of the same total duration. The first 0.5 nanoseconds (ns) of each trajectory was discarded and next 1.6 ns used for analysis. Conformations from each of the 50, 1.6 ns, trajectories were pooled to give a total effective simulation time of 80 ns. These 80 000 conformations were used as a structural pool for the 'selection' phase of the select-and-sample strategy (SAS, see below). The same protocol used for HIV-1 TAR, was used to prepare, equilibrate and produce the MD trajectories for HIV-2 TAR, except that a 33 Å sphere of TIP3 water was used to solvate the system.

RDC-Based SAS

Previous studies involving NMR analysis of protein structures used $S^2$ NH spin relaxation order parameters to select structural ensembles for a series of protein systems. In the present disclosure, the SAS approach can be adapted to allow use of RDC data which probe the orientational dynamics of individual bond vectors over timescales extending up to milliseconds (ms). In the SAS approach, MD is used to generate a set of conformations for the system of interest. One then searches for a 100 N-membered subset of structures that minimizes a cost function. Specifically, an N-membered subset of structures is randomly selected from a total pool of M structures and an initial_2-value is evaluated using Equation 1. Next, one of the N-membered structures is randomly chosen and replaced, by a random structure from the remaining M–N conformational pool. The 'move' from step k to k+1 is then accepted if $\chi^2_{(k+1)} < \chi^2_{(k)}$. If $\chi^2_{(k+1)} > \chi^2_{(k)}$, the move is accepted with a probability $P = \exp((\chi^2_{(k)} - \chi^2_{(k)} - \chi^2_{(k+1)})/T_{eff})$, where $T_{eff}$ is an effective temperature that is linearly decreased in a simulated annealing scheme. The cost function is $$\chi^2 = L^{-1} \sum_i^L (D_{ij}^{cal} - D_{ij}^{exp})^2 \quad (1)$$

Where $D_{ij}^{cal}$ and $D_{ij}^{exp}$ are the calculated and measured RDCs, respectively, L is the total number bond vectors, and $D_{ij}^{cal}$ is calculated using, $$D_{ij}^{cal} = \frac{\mu_0 \gamma_i \gamma_j \hbar}{4\pi^2 \langle r_{ij}^3 \rangle} \left\langle \frac{3\cos^2\theta - 1}{2} \right\rangle \quad (2)$$

where γi is the gyromagnetic ratio of the i-th nucleus, $r_{ij}$ is the bond length, θ is the angle between the bond vector and the external magnetic field and the angular brackets denote a time-average over all sampled orientations. The time-averaged angular term can be expressed in terms of the time-independent orientation of an internuclear vector relative to an arbitrary frame and the five order tensor elements (Sk1).

$$\left\langle \frac{3\cos^2\theta - 1}{2} \right\rangle = \sum_{kl=xyz} S_{kl} \cos(\alpha_k)\cos(\alpha_l) \quad (3)$$

where $\alpha_n$ is the angle between the internuclear vector and the $n^{th}$ axis of the arbitrary frame. Equation 3 assumes that internal motions do not affect overall alignment of the molecule.

This assumption can break down in RNA because collective motions of helical domains can lead to large changes in the overall shape and thus overall 2D alignment of the molecule. This can make it impossible to accurately compute $D_{ij}^{cal}$ for a given ensemble and thus to use RDCs in selecting conformers form an MD trajectory. Domain-elongation allows one to overcome this problem by rendering the overall shape of the 5 molecule far less sensitive to internal motions. Elongation also predefines the overall order tensor to be axially determined with principal direction oriented approximately parallel to axis of the elongated helix. This overall order tensor can be conveniently determined experimentally using RDCs measured in the elongated helix having one or more kinked sequences.

TAR ensembles by RDC-based SAS. The SAS RDC approach can be implemented with programs written in C++. 47 and 35 one-bond base and sugar C-H RDCs measured in EI-TAR and EII-TAR, respectively are used independently or in combination to select an HIV-1 TAR structural ensemble from a pool of 80 000 conformers derived from the combined 80 ns MD trajectory. For HIV-2 TAR, 35 RDCs measured in EI-TAR are used. Note that although RDCs can be measured on a TAR construct in which the apical loop is replaced by a UUCG loop, a detailed NMR study shows that this apical loop replacement does not affect inter-helical motions or local motions at the TAR bulge. When used in combination, both the EI-TAR and EII-TAR sets of RDCs are used (L=47+35=82) in computing the $\chi^2$ in Equation 1. In all cases, the overall alignment tensor can be assumed to be axially symmetric ($\eta$=0) with principal direction ($S_{zz}$) oriented parallel to the elongated helix axis as computed using the computer program CURVES. The magnitude of $S_{zz}$ can be obtained from an order tensor analysis.

Each RDC-SAS run can be initiated from N randomly selected conformers. A Monte Carlo (MC) simulated annealing scheme is then used to minimize the cost in Equation 1 as described above. Simulations are started at a high-effective temperature, where the MC acceptance probability is high (~0.99), and slowly decreased until the MC acceptance probability is ~$10^{-5}$. At a given effective temperature $10^5$ MC steps are carried out. The effective temperature ias then decreased, with $T_{i+1=0.9}$ $T_i$. The same protocol can be used for HIV-2 TAR, except that only 35 RDCs measured in the helix I elongated sample are used in the SAS analysis. Here, there is less motivation to acquire an additional set of helix II elongated RDCs given the near linear alignment of the two helices which renders the two sets of data degenerate.

Analysis of the SAS-derived TAR ensemble. The base angles, buckle ($\kappa$), opening ($\sigma$), propeller twist ($\omega$) and twist ($\Omega$), are calculated for eight non-terminal base pairs for each of the SAS selected TAR conformers using the computer program 3DNA. The inter-helical Euler angles $\alpha_h$, $\beta_h$ and $\gamma_h$ can be computed for each member of the ensemble, using the lower helix as a reference. Note that degenerate sets of Euler angles reflect the same inter-helical orientation and care can be taken in selecting among 60 degenerate angles to avoid non-realistic correlations.

SAS Analysis of HIV-1 E-TAR RDCs.

The RDCs measured previously in EII-TAR and EII-TAR are compared with those predicted based 65 on the combined 50×1.6=80 ns MD trajectory. Though some correlation is observed between the measured and predicted RDCs for both EI-TAR and EII-TAR, the deviations, expressed as root-mean-square-derivation (RMSD), ranging between 13 and 16 Hz, remains substantially larger than the estimated RDC measurement uncertainty (~4 Hz). The MD trajectory does not systematically under- or over-estimate the RDCs measured throughout the RNA, indicating that it does not significantly over or underestimate the amplitude of motions present. This is the case even though the RDC timescale sensitivity to motions (less than a millisecond) is greater than that of MD (~80 ns). Thus, it appears that the motions in TAR saturate at the nanosecond timescales consistent with relaxation dispersion studies that provide no evidence for ms-ms motions in 80 the stem-bulge-stem element of TAR.

Next, SAS can be used to pull out subensembles from the MD trajectory that satisfy the measured RDCs. A series of SAS runs are conducted with various ensemble sizes of N=5, 10, 20, 30, 40, 50 and 100. Comparing the RMSD between measured and predicted RDCs when combining the EI-TAR and EII-TAR RDCs as a function of N, gives a minimum RMSD at N=20. Increasing the ensemble size beyond N=20 does not lead to significant improvements in the fit and in fact a deterioration can be observed for N>20. This is likely due to sampling problems during the MC simulating annealing minimization of the cost function as the number of possible combinations increases steeply with N and the cost function exhibits, due to the frustration stemming from the underdetermined nature of the problem, a vast number local minima. An ensemble size of N=20 can be used in all subsequent SAS runs.

The RDCs calculated using a 20-member ensemble selected using the SAS approach exhibit a markedly 100 improved fit to the EI-TAR(RMSD=1.7 Hz), EII-TAR (RMSD=3.4 Hz) and EI-TAR+EII-TAR(RMSD=4.8 Hz) RDCs as compared to those calculated from the entire MD trajectory. Importantly, sub-ensembles can be determined that simultaneously reproduce the EI-TAR and EII-TAR RDCs with an RMSD (4.8 Hz) that is comparable to the estimated experimental RDC uncertainty (~4 Hz). The SAS selected conformers also did not lead to any steric collisions with the elongated helices for both EI-TAR and EII-TAR despite the fact that the helices were not actually elongated in the MD simulations.

To examine the uniqueness of the selected TAR ensemble, 100 independent N=20 SAS runs are carried out. Here, a maximum of 2000 unique snapshots can be selected. However, repeated runs can result in selection of a narrow set of similar conformations. The total number of unique snapshots selected by the RDC-SAS optimization algorithm is 422, 48 and 121 for EI-TAR, EII-TAR and EI-TAR+EII-TAR RDCs, respectively. Thus, the RDC data favors selection of specific conformations from the available pool. The conformers selected do vary when changing the value N. However, the overall distribution of conformations remains similar.

Local Motions in the Helices and Bulge

For the majority of the residues of 121 unique TAR conformers obtained from 100 N=20 SAS runs, very good agreement can be observed between the SAS ensemble and canonical values. Large deviations are however observed for the junctional A22-U40 base-pair, which in the MD simulation frequently deviates from a hydrogen bonded alignment. This is in excellent agreement with previous NMR data and studies showing that while the junctional G26-C39 base-pair forms a detectable hydrogen bond, the A22-U40 base-pair is flexible and does not form the expected base-pair in HIV-1 TAR.

The bulge residues exhibit different levels of motions. The highly conserved U23 bulge stacks onto A22 in the majority of the conformations, consistent with observation of NOE connectivity between A22 and U23. The two residues undergo limited motions consistent with previous $^{13}$C relaxation studies of dynamics in elongated HIV-1 TAR. Interestingly, select conformations exist in which U23 adopts a looped out conformation as observed in several ligand bound TAR structures (PDB ID#1QD3, 1UTS, and 397D). In contrast, residues C24 and U25 predominantly exist in a looped out conformation and are significantly more flexible, again in agreement with the previous carbon relaxation studies.

Collective Motions of Helices

The relative orientation of two helices i and j can be defined using three inter-helical Euler angles that describe the twist angle $\alpha_h$ about helix i, the inter-helix bend angle $\beta_h$, and the twist angle $\gamma_h$ about helix j. The three inter-helical Euler angles were computed for the 121 SAS selected TAR conformers and compared them to angles obtained for the entire MD trajectory. The MD trajectory spans a large range of inter-helical angles and the SAS conformers are widely distributed across the MD trajectory. For both the MD trajectory and SAS ensembles, significant correlation is observed between the three inter-helical angles, particularly between the twist angles $\alpha_h$ and $\gamma_h$. Such spatial correlations were reported previously based on a three-state rigid-body refinement of the TAR inter-helical orientation. The conformations obtained by SAS sample orientations that are in very good agreement with those obtained by a previous three-state analysis of the RDCs. The only significant deviations are observed in the $\alpha_h$-$\gamma_h$ plane for the near coaxial conformer ($\beta_h$~21°. This is not surprising given that for this near coaxial conformer, the RDCs measured in both EI-TAR and EII-TAR are highly insensitive to the twist angles $\alpha_h$ and $\gamma_h$.

The existence of any correlation between the geometry of base-pairs at the junction and the inter-helical bend angles is examined. The only significant observation is anti-correlation (R ~−0.70) between the basepair step angle ($\Omega$) at the G26-C39 junctional base-pair and $\alpha_h$ the twist angle about helix II. Thus, the unraveling of the G26-C39 base-pair may give rise to twisting motions around the axis of helix II.

Comparison with HIV-2 TAR Motions

The SAS approach can be used to analyze RDCs previously measured in HIV-2 EI-TAR in which the bulge residue C24 is omitted. Poor agreement (RMSD=15.1 Hz) is again observed between the measured EI-TAR RDCs and values computed using entire MD trajectory. By using SAS, an N=20 sub-ensemble that yields an RMSD of 1.7 Hz is found. Compared to HIV-1 TAR, repeated SAS runs results in selection of a larger number (276) of unique conformers for HIV-2 TAR. This could be attributed to a smaller RDC sensitivity to twisting motions both because the HIV-2 TAR structure is more linear and because only RDCs measured in EI-TAR was available for analysis.

Comparison of the SAS selected HIV-2 TAR conformers with those obtained for HIV-1 TAR reveals that reducing the length of the bulge in HIV-2 TAR leads to a marked decrease in the local motions in the junctional A22-U40 base-pair. In HIV-1, the SDs are approximately 30°, 45°, 13°, 16° for the base angles $\kappa$, $\sigma$, $\omega$ and $\Omega$, respectively. In HIV-2, they reduce to 10°, 6°, 8° and 6°, respectively. In contrast, significant static deviations in the opening angle for the G26-C39 junctional base pair are observed. Likewise, a significant reduction is observed in the local dynamics of bulge residues U23 and C25. U23 is less flexible and forms more stable stacking interactions on an also less flexible A22. The root mean square fluctuations (r.m.s.f.) of the atomic positions of U23 and U25 decrease from 1.89 Å and 3.49 Å, respectively in HIV-1 TAR to 1.45 Å and 1.49 Å, respectively in

HIV-2 TAR.

The reduction in the local motions in and around the bulge linker is as expected, accompanied by a reduction in the inter-helical motional amplitudes. Such a reduction is clearly observed for the inter-helical bending which decreases in standard deviation from ~33° to ~12°. This is in agreement with an order tensor analysis of RDCs, which reported a reduction in the $v_{int}$ (which ranges between 0 and 1 for maximum and minimum inter-helical motional amplitudes, respectively) from 0.45±0.05 to 0.77±0.04. The HIV-2 conformers cluster more tightly around more linear ($\beta_h$~0°) conformations. While a significant reduction in the amplitude of twisting motions about the two helices ($\alpha_h$ and $\gamma_h$) in HIV-2 is not observed, the RDC sensitivity to these angles is diminished in HIV-2 TAR both because the structure is on average more linear and because RDCs were only measured on the domain I elongated construct. Nevertheless, a stronger correlation between the twisting motions indicating that the $\alpha_h$ and $\gamma_h$ correlations originates in part from the steric drag one helix exerts on the other was observed.

Dynamics and Adaptive Recognition of Ligands

Numerous studies have shown that HIV-1 TAR undergoes large conformational rearrangements that allow binding of diverse targets in and around the bulge, including peptide derivatives of its cognate protein Tat, divalent ions, and five chemically distinct small molecules. The three inter-helical conformers obtained by a three-state ensemble analysis of RDCs measured in unbound TAR revealed a global inter-helical motional trajectory that encapsulated many of the ligand bound conformations. The SAS selected inter-helical conformers trace orientations similar to the ligand-bound TAR conformations, supporting the notion that unbound TAR can dynamically access its ligand-bound global conformations.

The SAS dynamical ensembles also allows one to examine to what extent are local features of the ligand binding pocket dynamically preformed in the absence of ligands. In general, the largest deviations are seen for the highly flexible residues C24 and U25, which are also known to be flexible in many of the ligand bound TAR conformations. Overall, these results suggest that local dynamics in an around the TAR bulge likely facilitate formation of the ligand binding pocket.

RNA Elongation provides a reliable approach for computing time-averaged RDCs in highly flexible RNAs providing a basis for integration with MD as shown here using the SAS approach. That the measured RDCs in both HIV-1 and HIV-2 can be satisfied using conformers selected from the MD trajectory suggests that neither HIV-1 nor HIV-2 TAR undergo significant ms-ms motions that are not sampled in the MD trajectory. This is consistent with relaxation dispersion NMR studies of HIV-1 TAR which provide no evidence for ms-ms motions in and around the bulge. In further support of this idea comes the observation that the first few low frequency eigenmodes of quasiharmonic motion obtained by principal component analysis of the 80,000 snapshots capture the dynamics as described by the SAS ensemble. However, it should also be noted that the SAS conformers can represent a 'discrete' approximation to what is more likely a continuous complex distribution of many more conformations. The SAS conformers can be thought of as discrete points along the configuration space that may help define salient features of the motional trajectory. Averaging over such a discrete number of conformers leads to efficient averaging of the RDCs. A correspondingly larger continuous distribution of many more conformations may be useful to accomplish the same level of motional averaging. It is therefore not surprising that the MD trajectory evolves outside the envelope defined by the SAS conformers and that the SAS envelope increases with the size of the ensemble. Thus, the most likely source of discrepancy between the measured RDCs and the MD simulation is the assignment of the relative weights to the various conformers.

RDC studies of partially unfolded proteins have emphasized the exquisite sensitivity of RDCs to the underlying conformational distribution.

The comparison of the dynamical ensembles generated for HIV-1 and HIV-2 TAR provided fundamental new insights into the dependence of RNA dynamics on the bulge length. As would be expected, reducing the length of the HIV-1 trinucleotide bulge by a single nucleotide (HIV-2) can lead to a significant reduction in the local motions in and around the bulge, as well as global inter-helical motions. In both HIV-1 and HIV-2, spatial correlations between twisting motions about individual helices, and to a lesser extent between twisting and bending as first reported based on the three-state ensemble analysis of the RDCs are observed. Importantly, the spatial correlations between the twisting motions increase significantly in HIV-2 TAR. This is expected if one were to consider limiting cases for the bulge length; at the limit of not having a bulge linker, the twisting dynamics becomes perfectly correlated, whereas for an infinitely long bulge, one would expect little correlation. The HIV-1 TAR dynamical ensemble allows direct examination of whether unbound TAR dynamically samples diverse ligand-bound conformations that have been reported to date. The methods and results discussed herein suggest that many of the key features of the ligand bound TAR conformations, including the global inter-helical orientation and local aspects of the ligand-binding pocket appear to be dynamically preformed in unbound TAR. However, a detailed comparison of the SAS conformations and the ligand bound TAR structures remains complicated by a number of factors. As mentioned above, the SAS conformers only represent an approximate discrete state ensemble to what is likely a more continuous conformational distribution. One also has to consider the uncertainty in ligand bound TAR structures, both due to experimental imprecision and because the ligand bound states may be flexible themselves.

Previous NMR studies reveal significant mobility in the TAR bulge, especially residues C24 and U25 when in complex with argininamide and $Mg^{2+}$. The ACP bound TAR structure also exhibits a large degree of inter-helical motions. Notwithstanding these complications, the results presented herein suggest that local dynamics in and around the bulge together with global motions of helices can drive much of the conformational adaptation required to bind to different ligand targets. The results presented herein also suggest that some of the TAR conformational changes require ligand binding to occur efficiently. For example, the key U38-A27•U23 base-triple in either of the HIV-1 or HIV-2 SAS conformers that is known to form in the TAR-argininamide complex is not observed. In this regard, it is interesting to note that larger deviations between the SAS and ligand bound conformations are generally observed for the weaker binding ligands and vice versa. It is possible that the weaker binding ligands expend a greater fraction of the binding energy changing the TAR conformation.

Example 2

Constructing Atomic-Resolution RNA Structural Ensembles Using MD and Motionally Decoupled NMR RDCs (See also: Al-Hashimi, H. M. et al., Methods, Constructing Atomic-Resolution RNA Structural Ensembles Using MD and Motionally Decoupled NMR RDCs, 37(10: 3670-9 2009; the contents of which is herein incorporated by reference in its entirety.)

2. Description of Method 2.1 Interpretation of RDCs Measured in Elongated RNA (E-RNA)

RDCs arise due to incomplete averaging of the dipolar interaction in partially aligned molecules. An expression (in Hz) for the dipolar coupling ($D_{ij}$) between two directly bonded spin ½ nuclei (i and j) is given by $$D_{ij} = -\frac{\mu_o \gamma_i \gamma_j h}{4\pi^2 r_{ij,eff}^3} \left\langle \frac{3\cos^2\theta - 1}{2} \right\rangle, \quad (4)$$

where $\mu_o$ is the magnetic permittivity of vacuum, h is Planck's constant, $r_{ij}$ is the inter-nuclear distance between the spins, and $\gamma$ is the gyromagnetic ratio. The angular term in Equation (4) is a function of the angle $\theta$ between the inter-nuclear vector and the applied magnetic field. The angular bracket denotes a time average over all angles sampled by the inter-nuclear vector due to both overall motions and internal motions occurring at timescales shorter than the inverse of the dipolar interaction (<ms). An effective bond length, $r_{ij,\ eff}$, subsumes the effects of distance averaging.

Motional averaging will generally reduce the value of the angular term $$\left\langle \frac{3\cos^2\theta - 1}{2} \right\rangle$$

and thus the magnitude of observed dipolar couplings (which can be on the order of kHz for non-reorienting directly bonded spins). When overall tumbling is random, the angular term averages to zero, and dipolar couplings are not observed under solution conditions. However, if a degree of alignment can be imparted on the solute of interest, the angular term will no longer average to zero. The greater the degree of alignment the greater the value of the angular term and magnitude of observed dipolar couplings. As is the case for through bond scalar couplings (J), through space dipolar couplings (D) effectively increase or decrease the average magnetic field at a given nucleus, resulting in splitting of resonances. Dipolar couplings are therefore often measured as new contributions to scalar couplings (J) that are observed under conditions of molecular alignment (J+D).

Use of RDCs in constructing RNA structural ensembles requires the ability to predict RDCs for a given proposed structural ensemble in which conformers interconvert at timescales shorter than the inverse of the dipolar interaction. This task is considerably simplified when one can (i) assume that internal motions are not correlated to overall alignment (the so-called "decoupling approximation") and (ii) determine the overall order or alignment tensor governing partial alignment of the molecule. Studies have shown that the decoupling approximation does not always hold for highly flexible and extended nucleic acid structures. In particular, changes in the relative orientation of helical domains can result in large changes in the overall RNA shape, which can in turn alter overall alignment of the molecule relative to the magnetic field. The ensuing breakdown in the decoupling approximation can make it difficult if not impossible to compute RDCs for a proposed structural ensemble.

One approach to overcome this problem is to elongate a target helix such that the overall RNA shape and hence its overall alignment is dominated by the elongated helix and is no longer as sensitive to internal motions occurring elsewhere in the molecule. The elongation also serves to predefine the overall order tensor to be axially symmetric with principal direction oriented nearly parallel to the axis of the elongated helix. The RDCs measured in the elongated helix can be used to experimentally determine the overall order tensor ($S_{kl}$). Thus, the time-averaged angular term in Equation (4) can be expressed for the $n^{th}$ conformer in terms of the time-independent orientation of an inter-nuclear vector relative to an arbitrary frame ($\alpha_i$) and the five order tensor elements ($S_{kl}$) describing overall alignment, $$\left\langle \frac{3\cos^2\theta - 1}{2} \right\rangle_n = \sum_{kl=xyz} S_{kl}\cos(\alpha_k^n)\cos(\alpha_l^n), \quad (5)$$

where $\alpha_m^n$ is the angle between the inter-nuclear vector in the $n^{th}$ conformer and the $m^{th}$ axis of the arbitrary frame. For a structural ensemble consisting of N conformers that interconvert at timescales shorter than the inverse of the dipolar interaction (<ms), the observed RDCs will be a population-weighted average over the ensemble, $$\langle D_{ij} \rangle = \sum_n^N p_n D_{ij}^n \quad (6)$$

A number of factors make RDCs ideal data for generating structural ensembles. First, RDCs provide long-range orientational constraints on individual bond vectors and thus provide information at the site-specific level. Second, RDCs measured in elongated RNA can be computed for a given structural ensemble with a high degree of accuracy. Third, RDCs are sensitive to internal motions spanning a broad range of timescales (<ms) and the ensembles generated will therefore sample a broad conformational distribution. Finally, RDCs can be measured with great abundance over different regions of the RNA structure and with the high density needed to construct multi-conformer ensembles.

2.2 Design of "NMR Invisible" Elongated RNA

The elongation of an RNA target is typically preformed by extending the length of a terminal helix using a stretch of Watson-Crick base-pairs. To avoid increasing spectral overlap due to elongation residues, an isotopic labeling strategy is used to render elongation residues "NMR invisible". Here, two constructs are prepared in which stretches of alternating unlabelled A-U/U-A (E-AU-RNA) and G-C/C-G (E-GC-RNA) base-pairs are employed for elongation using otherwise uniformly $^{13}C/^{15}N$ labeled G-C and A-U nucleotides, respectively. Two G-C base pairs must be added to the terminal end of E-AU-RNA to facilitate RNA synthesis by in vitro transcription. Structure prediction software such as mfold 3.3 are used to ensure that no alternate structures form as the result of elongation. The two constructs thus allow acquisition of NMR data over the entire RNA target while keeping elongation residues "NMR invisible".

One must ensure that the elongation does not perturb the structural and functional integrity of the RNA. This can be conveniently done by comparing spectra of elongated and non-elongated RNA samples. In general, elongation of terminal helices is not expected to give rise to significant RNA structural perturbations. However, depending on the RNA context, elongation of other non-terminal helices, which can allow the measurement of independent sets of RDCs (and RCSAs) that can be applied to generate structural dynamics with enhanced spatial resolution, may cause unwanted perturbations and should be carefully analyzed.

The degree of helix elongation needed to sufficiently decouple internal and overall motions will vary depending on the RNA target. In general, the elongation should render a target helix at least 4-5-fold longer than other helices in the RNA. If a structure for the RNA target is available, one can perform simulations using programs such as PALES, using idealized A-form helices to model the elongated helix, to examine the degree of motional coupling. In these simulations, one computes the variance in the predicted overall alignment tensor relative to the elongated helix as a function of varying the relative orientation of other shorter helices in the RNA. In general, the principal direction of order ($S_{zz}$) should not vary more than ±7 degrees about the elongated axis and the asymmetry ($\eta$) should always be <0.15. The secondary structure of an E-RNA construct should be verified using a secondary structure prediction programs such as mfold 3.3 to make sure that no alternative secondary structures can form.

The E-RNA NMR samples (>0.2 mM) are prepared using standard in vitro transcription reactions employing the appropriately $^{13}C/^{15}N$ labeled nucleotides. Formation of the elongated helix can be verified using NMR. First, one expects to observe an intense $^1H$ signal corresponding to the chemically degenerate Watson-Crick hydrogen bonded imino protons of guanines and uridines used in the elongation in 1D $^1H$ spectra. Second, one expects to observe signals that are characteristic of sequential $^{13}C/^{15}N$ enriched terminal GC base-pairs in the elongated helix, which are included to enhance transcription efficiency.

2.3 Partial Alignment of E-RNA

The measurement of RDCs in solution NMR is contingent upon inducing an appropriate degree of alignment typically on the order of $10^{-3}$. These levels of alignment can now be routinely achieved by dissolving biomolecules in inert ordered media that transmit some of their order to solute molecules through mechanisms that are believed to involve a combination of steric obstruction and charge-charge interactions. The most popular and commercially available ordering medium is Pf1 phage. Relative to other media, Pf1 phage is tolerant to the high salt concentrations used in nucleic acid samples and is negatively charged thus reducing the possibility for adverse inter-molecular interactions. Pf1 phage is available commercially or can be prepared using the methods described in reference. Typically, a Pf1 solution is exchanged into NMR buffer by repeated (at least three) rounds of ultra-centrifugation (1 hr in a Beckman TLA-100.3 rotor at 95,000 rpm, or 3-6 hrs in a VTi50 rotor at 40,000 rpm) followed by re-suspension of the pellet into the NMR buffer. Alternatively, one can dialyze Pf1 phage into the desired buffer. After completing the aligned experiments, the same ultracentrifugation procedure can in principle be used to recover the nucleic acid (supernatant) from the phage solution (pellet). Note that it will generally be difficult to achieve perfect separation of the nucleic acid sample from the phage medium.

Owing to their large structural anisotropy, the concentration of Pf1 phage needed to align E-RNA samples (~6-8 mg/ml) is usually considerably smaller than for non-elongated RNA (~20-25 mg/ml). If a model structure for the RNA is available, programs for predicting steric alignment such as PALES can be used to assess relative levels of order and the Pf1 phage concentration be adjusted accordingly. The aligned RNA sample is typically prepared by adding a pre-concentrated RNA solution (~0.5-1.5 mM) in NMR buffer to a desired volume of Pf1 phage (50 mg/mL) in NMR buffer in an Eppendorf tube and the sample gently transferred into the NMR tube avoiding formation of bubbles. One can to verify that the ordering medium does not interfere with the RNA conformation by comparing chemical shifts obtained in the unaligned and aligned samples. Note that small variations in the chemical shifts of nucleobase carbons and nitrogens are expected between unaligned and aligned samples due to incomplete averaging of Residual Chemical Shift Anisotropies (RCSAs). These RCSA contributions scale linearly with the magnetic field and degree of order.

2.4 Measurement of RDCs in E-RNA

A large number of pulse sequences have been reported for the measurement of a wide variety of RDCs in nucleic acids. These experiments are not described in detail here as they have been reviewed elsewhere. The RDCs are generally computed from the difference in splittings observed in the absence (J) and presence of alignment media (J+D). For large E-RNA, it is important to employ TROSY schemes for measuring RDCs in the nucleobases. For example, CH splittings in the nucleobases are measured as the difference between the upfield and downfield components of the $^1H$-$^{13}C$ doublet along the $^1H$ dimension using the narrow TROSY component in the $^{13}C$ dimension. For E-RNA, the most commonly targeted RDCs are those between directly bonded C—H and N—H nuclei (e.g. $C_2H_2/C_8H_8$ of the adenine and guanine bases, $C_5H_5/C_6H_6$ of the uracil and cytosine bases, $N_1H_1$ and $N_3H_3$ of the guanine and uracil bases, and $C_1'H_1'$ of the ribose), which yield the largest RDC magnitudes. While additional one, two, and three bond RDCs can also be measured, these RDCs are smaller and may prove difficult to measure in larger E-RNAs (>60 nt).

When using frequency domain experiments to measure splittings, phase distortions due to improper calibration of timing delays and/or imperfections in shaped pulses can yield splitting measurement errors that are larger than theoretical limits (approximately given by 0.7*Linewidth*(1/Signal: Noise)). To avoid differential contributions from magnetic field induced RDCs and relaxation interference effects, splittings in unaligned and aligned samples should be measured at the same magnetic field strength. It is advisable to estimate the experimental RDC uncertainty from the standard deviation in duplicate measurements. Resonances exhibiting significant differences (>3σ) as a result of considerable broadening, overlap, presence/absence of unresolved multiplets should not be used in subsequent data analysis.

2.5 Normalizing RDCs Measured in Distinct E-RNA Samples

The RDCs measured in the different E-AU and E-GC samples can be normalized to take into account possible differences in the degree of alignment before the data can be pooled together and analyzed in constructing atomic-resolution ensembles. The normalization can be carried out using RDCs measured in contiguous Watson-Crick base-pairs, which can be modeled assuming an idealized A-form geometry (see below). The errors introduced due to A-form structural noise can be estimated according to known methods in the art. The normalization can be accomplished by repeatedly fitting the total pool of RDCs to individual idealized A-form helices following uniform scaling of the RDCs measured in one sample (typically the sample with the lesser number of measured RDCs) by a normalization factor L. The L value that minimizes the Quality factor (Q) is computed using:

$$Q = \sqrt{\frac{\sum w_i (D_i^{calc} - D_i^{exp})^2}{\sum w_i (D_i^{exp})^2}}. \quad (7)$$

Fitting of the RDCs to the A-form helices can be accomplished using various computer programs including ORDERTEN-SVD, REDCAT, PALES, iDC, CONFORMIST and RAMAH, which are freely available.

2.6 Determining the Overall Order Tensor

The interpretation of E-RNA RDCs can be greatly simplified by determining the overall order tensor governing alignment. The overall order tensor can be determined using RDCs measured in the reference elongated helix using a procedure that is briefly outlined below:

Build idealized A-form helices (PDB files) corresponding to the sequence of the reference helix. For example, to build an A-form helix using the Biopolymer module of Insight II 2000.1 (Molecular Simulations, Inc): click on the module icon in the upper left corner and select append from the nucleotide menu. In the pop-up box, select "A RNA Duplex". Input a name for the molecule into the text field. Next, select the appropriate Watson-Crick base-pair in the Nucleotide text field. Continue to append base-pairs—following along in sequence from 5' to 3'—until you have completed building the desired helix. Click cancel and then select the File menu and choose the desired export option for the helix coordinates. The idealized A-form helices should conform to published parameters. If building helices using INSIGHT II 2000.1 (Molecular Simulations, Inc.), care needs to be taken to correct the propeller twist angles to the proper value of −14.5°. The program, HPmod, can be used to correct for the improper propeller twist. Programs such as Curves 5.1, FreeHelix98, 3DNA, SCHNAaP, NUPARM and NUCGEN can be used to compute relevant helix parameters.

Compute five order tensor elements for each A-form helix by fitting the RDCs to the A-form PDB coordinates. Several programs are available to carry out such calculations including ORDERTEN-SVD, REDCAT, PALES, iDC, CONFORMIST and RAMAH. Note, non-ideal WC base-pairs are excluded from this analysis. In our lab RAMAH is used to determine the five order tensor elements.

Examine the correlation between measured and back-calculated RDCs. Major outliers should be interrogated for possible measurement errors.

Use AFORM-RDC or other approaches to estimate the order tensor error due to structural noise and RDC measurement uncertainty.

Owing to the uniform distribution of charge in polyanionic nucleic acids, the steric and electrostatic forces are believed to have a similar functional form. Consequently, E-RNAs are expected to align in ordering media with the principal direction of order ($S_{zz}$) oriented along the elongated axis. In general, one expects positive alignment ($S_{zz}>0$) with the $S_{zz}$ direction being, on average, oriented parallel to the magnetic field. The asymmetry of alignment is also expected to be nearly axially symmetric (η~0).

2.7 Molecular Dynamics (MD) Simulations of RNA

MD simulations are used in this case to generate a large conformational pool that can be filtered using experimental RDCs so as to generate a more accurate ensemble of RNA conformers. A variety of MD simulation packages and force-fields can be employed to simulate nucleic acids. Herein, a protocol for simulating RNA using the CHARMM MD package with force-field parameter set 27 for nucleic acids is described.

System Preparation using MMTSB Toolkit: To prepare the system for simulation with CHARMM, the Multiscale Modelling Tools for Structural Biology (MMTSB) Toolset available from the Scripps Research Institute and other academic institutions (http://blue11.bch.msu.edu/mmtsb/Main_Page) can be used. The MMTSB Toolset includes various program files and scripts to perform MD alone or in conjunction with other computer modeling software. The Toolset consists of a set of perl scripts that can be used to prepare, initiate and analyze a system for MD simulation. Here they are only described in terms of preparing a system for an MD simulation:

Obtain Coordinates for the RNA from the Protein Data Bank (PDB) or the Nucleic Acid Database (NDB).

Use the MMTSB toolset script convpdb.pl to add solvent and ions to the system using the command: convpdb.pl -solvate -cutoff 15 -cubic -ions SOD:27 hivtar-0.pdb>hivtar-0-solvated-ions.pdb. In this example -solvate flag indicates that pdb solvent molecules will be added, -cutoff 15 specifies the distance (15 Å) from the RNA to the edge of the solvent cube, -cubic specifies a solvent shape (alternatively a octahedron water box could be specified with -octahedron flag), -ions SOD:27 specifies that 27 sodium ions be added to make the system charge neutral, and hivtar-0.pdb indicates the input pdb file.

Use the MMTSB toolset script genPSF to generate protein structure file (PSF) and CHARMM formatted coordinate file using the command: genPSF.pl -par nodeoxy -crdout hivtar-0-solvated-ions.cor hivtar-0-solvated-ions.pdb>hivtar-0-solvated-ions.psf. Here the -par nodeoxy flag specifies that the system is an RNA molecule, -crdout and hivtar-0-solvated-ions.cor specifies the filename for the output CHARMM formatted coordinate, and is hivtar-0-solvated-ions.psf is the output PSF file.

Equilibration Using CHARMM

Read in parameter and topology file set 27 for nucleic acids.

Read in generate PSF and coordinates files.

Do 500 steps Steepest Descent (SD) minimization to remove bad contacts using the CHARMM MINI SD module.

Place harmonic constraints on heavy atoms of the RNA using CONS HARM (see CHARMM's cons.doc manual) and perform 1000 steps of SD minimization, followed by 2000 steps of Adopted Basis Newton-Raphson (ABNR) minimization or until energy converges (see CHARMM's minimiz.doc manual). This process allows solvent and counter-ions to relax around the RNA.

The energy minimized structure is heated up to 300 K, by carrying out a series of constant temperature simulations starting at 0 K for ~20 ps at each temperature. The temperature is increased by 25 K each incremental time-step using coordinates from the previous run as input for the next 20 ps simulation. The Nosé Hoover thermostat with a coupling constant of 100 ps$^{-1}$ together with the Velocity Verlet (VVER) integrator with a integration time-step of 1 fs can be used. Periodic boundary conditions are used, with electrostatics calculated using particle-mesh Ewald and Lenard-Jones interaction truncated at 12 Å, with a switching function applied between 10 to 12 Å.

At 300 K the harmonic constraint is gradually removed by decreasing the force constant.

Equilibration is continued at 300 K and without any harmonic constraints for an additional 500 ps.

Generation of trajectory: Generation of structural ensembles from an MD derived pool of conformations hinges on the ability to adequately sample the relevant regions of conformational space. It has been shown that using multiple short trajectories may enhance the rate of conformational sampling when compared to a single long trajectory of same effective length, which is advantageous to our methods since the experimental data is used to filter unrealistic conformations. In this protocol, the use of multiple short trajectories to generate such selection pools is described.

Initiate a set of independent MD constant temperature replica trajectories starting from the same equilibrated structure generated in part-A. 50 replicas have been found to be sufficient. The thermostat, integrator and non-bonded energy calculation options are same as stated above.

Assign each replica a different set of initial velocities by specifying a different seed value for the random number generator used to assign initial velocities using the ISEED input flag into DYNA.

Generate trajectories of about ~3 ns, while saving conformations each 1 ps.

Discard the first 1 ns and pool the remaining ~2 ns trajectories for each replica to create a selection pool. In this case ~100,000 were generated conformations. Use this pool for selection of structural ensembles as described below.

2.8 Combine NMR RDCs and MD to Generate a Structural Ensemble—Sample and Select

The Sample and Select method was originally implemented as a tool to generate structural ensembles of proteins using a combination of MD and NMR derived NH spin relaxation order parameters ($S^2$). The basic idea is to sample the relevant conformational space and then select a sub-ensemble that is most consistent with the experimental data. The method was adapted to use RDCs measured on E-RNA to select structural ensembles of RNA from a selection pool derived from an MD simulation. The SAS selection is preformed following the recently described procedure in which one minimizes a cost function utilizing a Monte-Carlo simulated annealing approach:

Randomly select an N-membered subset of structures from the total pool of M structures and calculate $\chi^2$ using $$\chi^2 = L^{-1} \sum_i^L (D_{ij}^{cal} - D_{ij}^{exp})^2 \qquad (8)$$

where $D_{ij}^{cal}$ and $D_{ij}^{exp}$ are the calculated and measured RDCs, respectively, and L is the total number of bond vectors.

Randomly replace one of the N-membered structures with a randomly chosen structure from the remaining M-N conformational pool. Accept the move for step k to k+1 if $\chi^2$(k+1)<$\chi^2$(k). If $\chi^2$(k+1)>$\chi^2$(k), accept the move with a probability $P = e^{((\chi^2(k)-\chi^2(k+1))/T_i)}$, where $T_i$ is the effective temperature. Typically, a linear cooling schedule is used, specifically $T_i+1 = 0.9\ T_i$, where the index i runs over the temperature increments.

Continue MC annealing simulations until $\chi^2$ converges. In our simulations with M=80000, N=20 and L=82, convergence was achieved within 100 temperature increments with each consisting of 100,000 MC steps.

As an example, the SAS approach together with RDCs measured in two elongated RNA samples are used to construct atomic-resolution ensembles for the HIV-1 transactivation response element (TAR). RDCs are measured in two elongated samples in which each domain was independently elongated. The RDCs measured previously in the two elongated TAR samples can be compared with those predicted based on the combined 50×1.6=80 ns MD trajectory. Though some correlation is observed between the measured and predicted RDCs, the deviations (RMSD ranging between 13-16 Hz) remains substantially larger than the estimated RDC measurement uncertainty (~4 Hz). The poor agreement indicates that the MD simulation does not accurately reproduce the TAR internal motions. This highlights the importance of including experimental data in the analysis of MD simulations. Using SAS, it is possible to select a sub-ensemble consisting of N=20 snap-shots from the MD trajectory that reproduce the RDCs close to within experimental precision. The SAS selected TAR structural ensemble reveals extensive local and global motions in TAR at atomic-resolution.

Once an ensemble is constructed, a method to determine its validity can be used. This can be done using experimental data that is not included in the selection process. In addition to RDCs, other data from RCSAs, NOEs, as well as spin relaxation order parameters, or data from other experimental techniques such as SHAPE foot printing data and fluorescence can be used to validate the ensemble. The constructed ensembles can also be compared with expected parameters. For example, average and standard deviations for various base angles have been reported for Watson-Crick base-pairs that are flanked by other Watson-Crick base-pairs in A-form helices. Last but not least, the ensemble can be interpreted in light of known mechanistic aspects of the RNA function.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method for analyzing structural conformations by identifying dominant conformers of a target effector molecule, the method comprising:
   a. providing a target effector molecule having an artificial elongated sequence comprising one or more variable kinks;
   b. obtaining residual anisotropic interaction and spin relaxation data from said target effector molecule having said elongated structure using nuclear magnetic resonance spectroscopy, X-ray crystallography or both;
   c. creating a plurality of atomic-resolution dynamical ensembles reflecting motional trajectories of said target effector molecule by constructing computational models of said target effector molecule using one or more computer modeling programs;
   d. selecting a plurality of dynamical sub-ensembles using a computational simulation algorithm to generate a plurality of conformers that satisfy said residual anisotropic interactions and spin relaxation data obtained in step b;
   e. identifying a plurality of dominant conformers from said dynamical ensembles; and
   f. selecting and outputting said dominant conformers and motional trajectories of said target effector molecule.

2. The method according to claim 1, wherein the target effector molecule is a polypeptide, a protein, a polysaccharide, a nucleic acid, a lipid, a glycoprotein, a glycolipid or a combination thereof.

3. The method according to claim 2, wherein the target effector molecule is a polysaccharide, a nucleic acid, a lipid, a glycolipid or a combination thereof.

4. The method according to claim 3, wherein the target effector molecule is a nucleic acid.

5. The method according to claim 4, wherein said target effector molecule is an RNA molecule having 2 to 1000 base pairs.

6. The method according to claim 1, wherein said one or more variable kinks in step 'a' is a section of said target effector molecule, said one or more variable kinks comprises a bulge, an internal loop, an n-way junction, or combinations thereof.

7. The method according to claim 6, wherein said one or more variable kinks vary from each other in at least one of sequence length, position of said kink in said target effector molecule or symmetry.

8. The method according to claim 6, wherein said internal loop is asymmetric or symmetric.

9. The method according to claim 1, wherein said computer modeling program used in step 'c' is Molecular Dynamics.

10. The method of claim 1, wherein step b is performed in the presence of a ligand, said ligand having an affinity for a recognition domain of said target effector molecule.

11. The method of claim 10, further comprising screening a plurality of ligands to rank the binding strength of each of said ligands with the plurality of computational models selected, having a root-mean square deviation below a predetermined threshold.

12. The method of claim 11, further comprising selecting one or more ligands based on their individual rank.

13. The method according to claim 10, wherein the computer modeling program used in step 'c' is Molecular Dynamics.

14. The method according to claim 10, wherein the ligand is a small organic molecule, a peptide, a polynucleotide, a carbohydrate and polymers thereof.

15. A computer configured to perform the method described in claim 1.

16. A computer system comprising a processor configured to perform a method of analyzing the structural conformations of a target effector molecule to determine the dominant conformers of the target effector molecule, by:
   a. generating a plurality of conformers from a plurality of dynamical sub-ensembles obtained using Monte Carlo simulation that satisfy residual anisotropic interaction and spin relaxation data obtained from said target effector molecule, having an elongated structure, using nuclear magnetic resonance spectroscopy, X-ray crystallography or both;
   b. identifying a plurality of dominant conformers from said dynamical ensembles; and
   c. selecting and outputting said dominant conformers and motional trajectories of said target effector molecule.

17. The computer system of claim 16, wherein said target effector molecule is in the presence of a ligand, said ligand having affinity for the active site of said target effector molecule, and wherein the conformations of the target effector molecule reveal the binding portion of the effector molecule to a putative ligand structure.

18. The computer system of claim 17, further designed to screen a plurality of ligands and rank the binding strength of each of said ligands with the plurality of computational models selected, having a root-mean square deviation below a predetermined threshold.

19. The computer system of claim 18, further designed to select one or more ligands based on their individual rank.

20. A method for analyzing the structural conformations of a target effector molecule by determining dominant conformers that can be targeted with a small molecule, the method comprising:
   a. providing a target effector molecule having an artificial elongated sequence having one or more variable kinks;
   b. obtaining residual anisotropic interactions and spin relaxation data experimentally from said target effector molecule having said elongated structure;
   c. creating a plurality of atomic-resolution dynamical ensembles reflecting motional trajectories of said target effector molecule;
   d. selecting a plurality of dynamical subensembles using Monte Carlo simulation to generate a plurality of conformers that satisfy said residual anisotropic interactions and spin relaxation data;
   e. identifying a plurality of dominant conformers from said dynamical ensembles that can be targeted by a small molecule; and
   f. selecting and outputting said dominant conformers and motional trajectories of said target effector molecule.

21. The method according to claim 20, wherein the target effector molecule is a polypeptide, a protein, a polysaccharide, a nucleic acid, a lipid, a glycoprotein, a glycolipid and combinations thereof.

22. The method according to claim 21, wherein the target effector molecule is a biologically active fragment of said polypeptide, a protein, a polysaccharide, a nucleic acid, a lipid, a glycoprotein, a glycolipid.

23. The method according to claim 20, wherein the variable kinks comprise a bulge, an internal loop, an n-way junction.

24. The method according to claim 23, wherein the variable kinks vary from each other in at least one of sequence length, position of kink in the target effector molecule and symmetry.

25. The method according to claim 23, wherein the internal loop is asymmetric or symmetric.

26. The method according to claim 20, wherein residual anisotropic interactions and spin relaxation data used in step (b) is X-ray crystallographic data.

27. The method according to claim 20, wherein the spin relaxation data used in step (b) is nuclear magnetic resonance data.

28. The method of claim 20, wherein the residual anisotropic interactions and spin relaxation data used in step (b) is X-ray crystallographic data and nuclear magnetic resonance data.

29. The method of claim 20, wherein the creating a plurality of atomic-resolution dynamical ensembles comprises constructing computational models of said target effector molecule using any one or more computer modeling programs comprising: Molecular Dynamics, Monte Carlo, CHARMM, FELIX, QUANTA and GrowMol.

* * * * *

UNITED STATES PATENT AND TRADEMARK OFFICE
CERTIFICATE OF CORRECTION

PATENT NO. : 8,498,823 B2
APPLICATION NO. : 13/120064
DATED : July 30, 2013
INVENTOR(S) : Hashim M. Al-Hashimi et al.

It is certified that error appears in the above-identified patent and that said Letters Patent is hereby corrected as shown below:

In the Specification

Column 24, Table 1, entry 8, line 1, delete "GG[YX]10" and insert --GG[YX]$_{10}$--.

Column 26, line 33, delete " $P=\exp((\chi^2_{(k)} - \chi^2_{(k)} - \chi^2_{(k+1)})/T_{eff})$," and insert -- $P=\exp((\chi^2_{(k)} - \chi^2_{(k+1)})/T_{eff})$, --.

Column 27, line 42, delete "$T_{i+1=0.9}T_i$." and insert --$T_{i+1}=0.9T_i$.--.

Column 29, line 24, delete "($\beta_h$~21°." and insert --($\beta_h$ ~21°).--.

Column 29, line 61, after "in", delete "¶".

Column 31, line 65, delete "37(10:" and insert --37(11):--.

Column 35, line 47, delete "(>3a)" and insert --(>3σ)--.

Column 35, line 67, delete "(O)" and insert --(Q)--.

Signed and Sealed this
Twenty-fourth Day of February, 2015

Michelle K. Lee
*Deputy Director of the United States Patent and Trademark Office*